US011903745B2

(12) United States Patent
 Kimura

(10) Patent No.: US 11,903,745 B2
(45) Date of Patent: *Feb. 20, 2024

(54) IMAGE PROCESSING APPARATUS

(71) Applicant: CANON MEDICAL SYSTEMS CORPORATION, Otawara (JP)

(72) Inventor: Tokunori Kimura, Yaita (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 3 days.

This patent is subject to a terminal disclaimer.

(21) Appl. No.: 17/692,421

(22) Filed: Mar. 11, 2022

(65) Prior Publication Data
 US 2022/0192608 A1 Jun. 23, 2022

Related U.S. Application Data

(63) Continuation of application No. 15/369,016, filed on Dec. 5, 2016, now Pat. No. 11,311,248.

(30) Foreign Application Priority Data

Dec. 14, 2015 (JP) .................................. 2015-243547

(51) Int. Cl.
 *A61B 5/00* (2006.01)
 *G06T 15/08* (2011.01)
 (Continued)

(52) U.S. Cl.
 CPC .......... *A61B 5/7282* (2013.01); *A61B 5/0042* (2013.01); *A61B 5/055* (2013.01);
 (Continued)

(58) Field of Classification Search
 CPC ..... A61B 5/7282; A61B 5/0042; A61B 5/055; A61B 5/4088; A61B 5/742;
 (Continued)

(56) References Cited

U.S. PATENT DOCUMENTS 8,886,283 B1 11/2014 Chen
2002/0070970 A1 6/2002 Wood
(Continued)

FOREIGN PATENT DOCUMENTS

JP 9-313461 A 12/1997
JP 2005-95340 A 4/2005
(Continued)

OTHER PUBLICATIONS

Hidekazu Tomimoto, "Vascular Dementia; Revisited", Journal of Senile dementia Research, 19(1), 2012, 5 pages (w/partial English translation).

(Continued)

*Primary Examiner* — Peter Luong
(74) *Attorney, Agent, or Firm* — Oblon, McClelland, Maier & Neustadt, L.L.P.

(57) ABSTRACT

An image processing apparatus according to an embodiment includes processing circuitry. The processing circuitry is configured to obtain three-dimensional image data of a brain acquired by performing a magnetic resonance imaging process. The processing circuitry is configured to generate a projection image rendering a micro bleed or calcification occurring in the brain by performing a projecting process on the three-dimensional image data in a range limited on the basis of a shape of the brain. The processing circuitry is configured to output the projection image.

21 Claims, 12 Drawing Sheets

(51) Int. Cl.
  *A61B 5/055* (2006.01)
  *G06T 11/00* (2006.01)

(52) U.S. Cl.
  CPC ............ *A61B 5/4088* (2013.01); *A61B 5/742* (2013.01); *G06T 11/003* (2013.01); *G06T 15/08* (2013.01); *A61B 2576/026* (2013.01); *G06T 2210/41* (2013.01)

(58) Field of Classification Search
  CPC . A61B 2576/026; G06T 11/003; G06T 15/08; G06T 2210/41; G16H 30/40
  See application file for complete search history.

(56) References Cited

U.S. PATENT DOCUMENTS

| | | |
|---|---|---|
| 2005/0119547 A1 | 6/2005 | Shastri |
| 2006/0262968 A1 | 11/2006 | Drobnitzky |
| 2010/0040264 A1 | 2/2010 | Volkau et al. |
| 2013/0221961 A1 | 8/2013 | Liu |
| 2014/0219533 A1 | 8/2014 | Sato et al. |
| 2016/0345925 A1 | 12/2016 | Westerhoff |

FOREIGN PATENT DOCUMENTS

| | | |
|---|---|---|
| JP | 2006-43200 | 2/2006 |
| JP | 2006-320387 A | 11/2006 |
| JP | 2010-12176 A | 1/2010 |
| JP | 2010-46473 A | 3/2010 |
| JP | 2012-85833 A | 5/2012 |
| JP | 2012-235934 A | 12/2012 |
| JP | 2013-59437 A | 4/2013 |
| WO | WO2013/054718 | 4/2013 |

OTHER PUBLICATIONS

Wiesje M. Van Der Flier, et al., "Microbleeds in vascular dementia: Clinical aspects", Experimental Gerontology, 47 (11), 2012, 5 pages.

Jeroen D.C. Goos, MD, et al., "Clinical Relevance of Improved Microbleed Detection by Susceptibility-Weighed Magnetic Resonance Imaging", Stroke, 42, 2011, 10 pages.

Japanese Office Action dated Sep. 3, 2019 in Japanese Patent Application No. 2015-243547, 3 pages.

Japanese Office Action dated Mar. 3, 2020 in Japanese Patent Application No. 2015-2413547, 4 pages.

| Area | # of MBs | Volume |
|------|----------|--------|
| A | 8 | 10/ 90 |
| B | 10 | 15/100 |
| C | 12 | 20/120 |

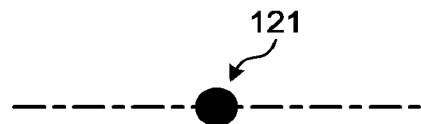
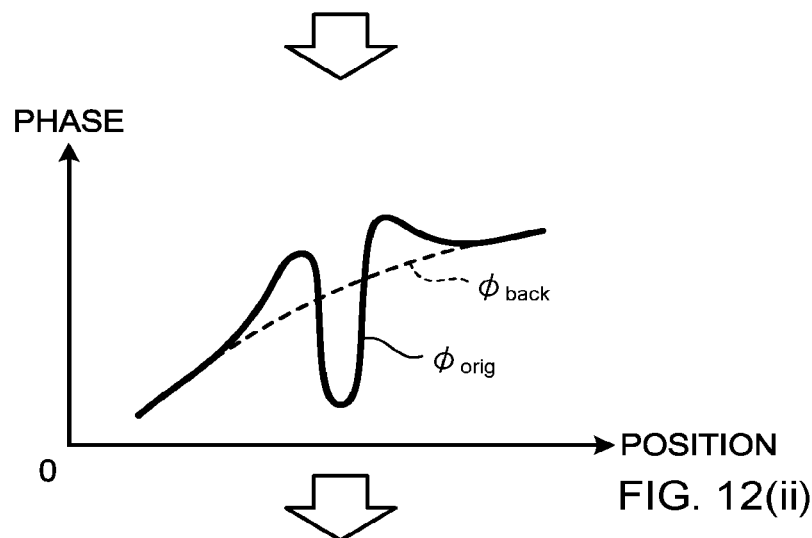
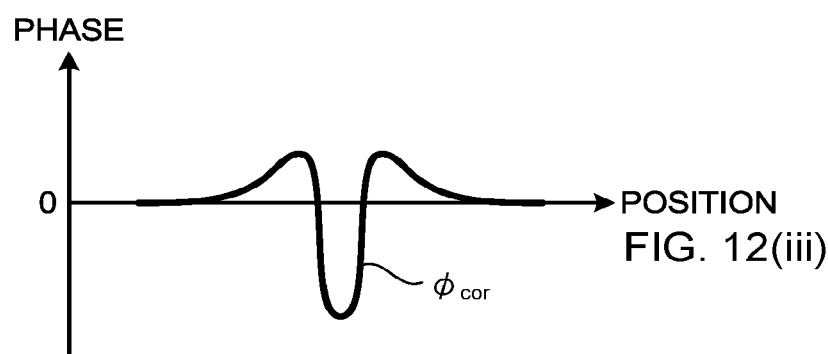
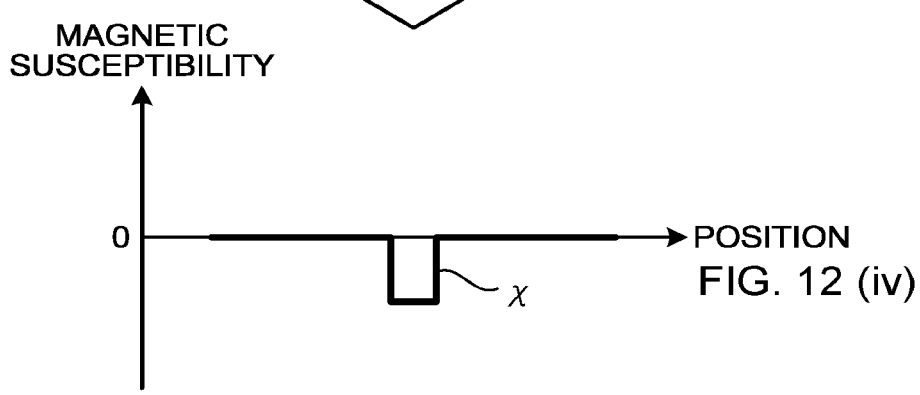

FIG. 13(i)
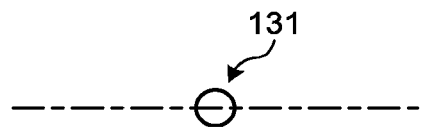
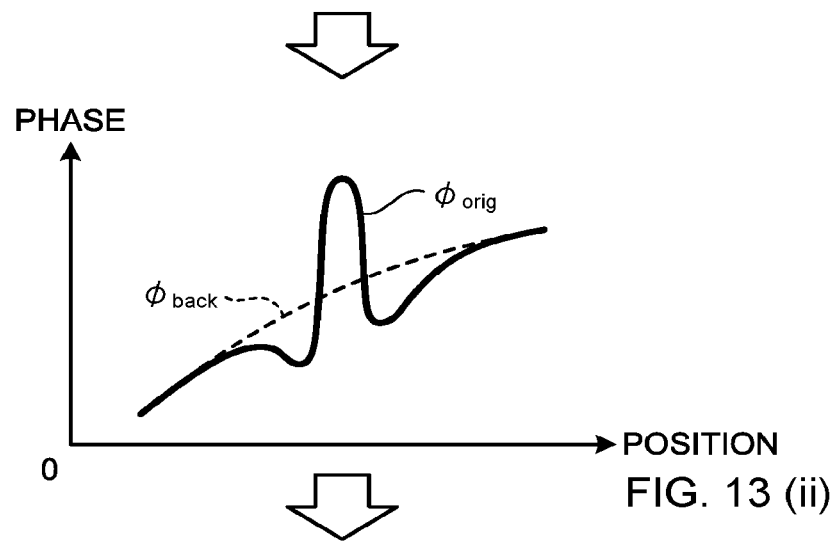
FIG. 13 (ii)
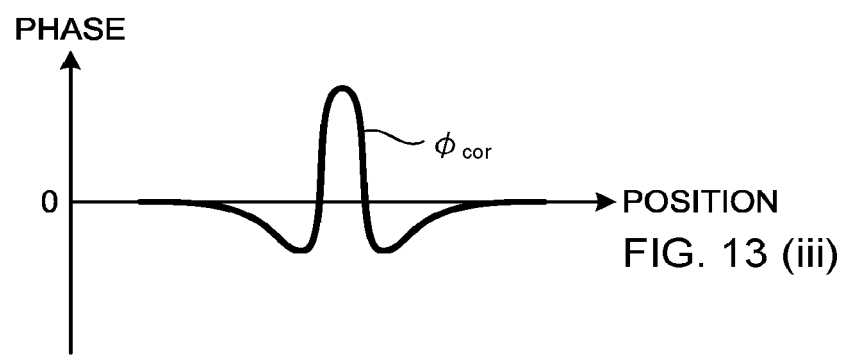
FIG. 13 (iii)
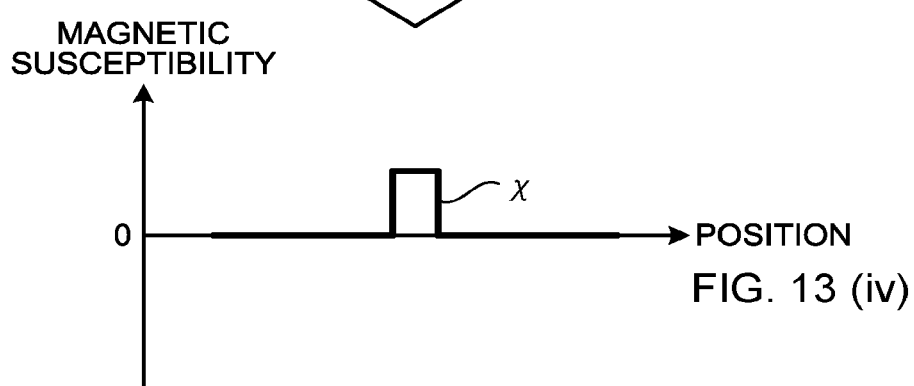
FIG. 13 (iv)

IMAGE PROCESSING APPARATUS

CROSS-REFERENCE TO RELATED APPLICATIONS

This application is a continuation of and claims the benefit of priority under 35 U.S.C. § 120 from U.S. application Ser. No. 15/369,016 filed Dec. 5, 2016, and claims the benefit of priority under 35 U.S.C. § 119 from Japanese Patent Application No. 2015-243547 filed Dec. 14, 2015; the entire contents of each of which are incorporated herein by reference.

FIELD

Embodiments described herein relate generally to an image processing apparatus.

BACKGROUND

Conventionally, dementia or the like is diagnosed in the brain by using various types of medical images generated by image diagnosis apparatuses. Examples of dementia include Alzheimer-type dementia and vascular dementia. It is known that Alzheimer-type dementia prominently exhibits atrophy of cerebral tissues and that vascular dementia prominently exhibits micro bleeds (MBs), in particular. Further, it has been reported that there is also mixed-type dementia that prominently exhibits both atrophy of cerebral tissues and MBs.

BRIEF DESCRIPTION OF THE DRAWINGS

FIGS. 12($i$) to 12($iv$) are drawings illustrating a process of enhancing the contrast of an MB performed by a projecting function according to a seventh modification example;

FIGS. 13($i$) to 13($iv$) are drawings illustrating a process of enhancing the contrast of a calcification site performed by the projecting function according to the seventh modification example.

DETAILED DESCRIPTION

An image processing apparatus according to an embodiment includes processing circuitry. The processing circuitry is configured to obtain three-dimensional image data of a brain acquired by performing a magnetic resonance imaging process. The processing circuitry is configured to generate a projection image rendering a micro bleed or calcification occurring in the brain by performing a projecting process on the three-dimensional image data in a range limited on the basis of a shape of the brain. The processing circuitry is configured to output the projection image.

First Embodiment

Figure 1:
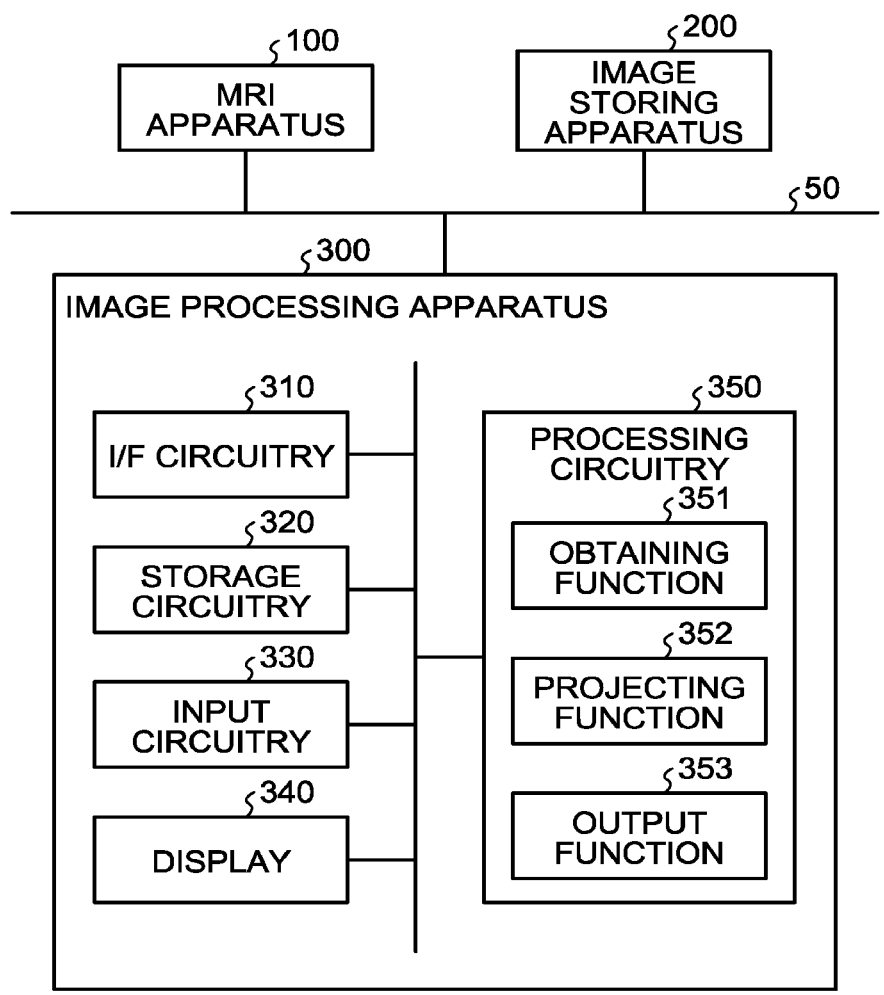
FIG. 1 is a diagram of an exemplary configuration of an image processing apparatus according to a first embodiment.

FIG. 1 is a diagram of an exemplary configuration of an image processing apparatus according to a first embodiment. For example, as illustrated in FIG. 1, an image processing apparatus 300 according to the first embodiment is connected, via a network 50, to a Magnetic Resonance Imaging (MRI) apparatus 100 and to an image storing apparatus 200. Also, the image processing apparatus 300 may further be connected, via the network 50, to one or more other image diagnosis apparatuses, such as an X-ray Computed Tomography (CT) apparatus, an ultrasound diagnosis apparatus, and/or a Positron Emission Tomography (PET) apparatus.

The MRI apparatus 100 is configured to acquire image data of an examined subject (hereinafter, "patient") by making use of magnetic resonance phenomena. More specifically, the MRI apparatus 100 acquires magnetic resonance data from the patient, by executing various types of image taking sequences on the basis of image taking conditions set by an operator. Further, the MRI apparatus 100 generates two-dimensional or three-dimensional image data by performing an image processing process such as a Fourier transform process on the acquired magnetic resonance data.

The image storing apparatus 200 is configured to store image data acquired by various types of image diagnosis apparatuses. For example, the image storing apparatus 200 obtains the image data from the MRI apparatus 100 via the network 50 and further stores the obtained image data into storage circuitry provided either inside or outside of the apparatus. For example, the image storing apparatus 200 is realized with a computer device such as a server apparatus.

The image processing apparatus 300 is configured to process the image data acquired by the various types of image diagnosis apparatuses. For example, the image processing apparatus 300 obtains the image data from either the MRI apparatus 100 or the image storing apparatus 200 via the network 50 and further stores the obtained image data into storage circuitry provided either inside or outside of the apparatus. Further, the image processing apparatus 300 performs various types of image processing processes on the obtained image data and outputs the image data either before or after the image processing processes to a display or the like.

For example, as illustrated in FIG. 1, the image processing apparatus 300 includes interface (I/F) circuitry 310, storage circuitry 320, input circuitry 330, a display 340, and processing circuitry 350.

The I/F circuitry 310 is configured to control transfer and communication of various types of data transmitted and received between the image processing apparatus 300 and another apparatus connected thereto via the network 50. For example, the I/F circuitry 310 is realized with a network card, a network adaptor, a Network Interface Controller (NIC), or the like. For example, the I/F circuitry 310 is connected to the processing circuitry 350, converts image data output from the processing circuitry 350 into image data in a format compliant with a predetermined communication protocol, and transmits the image data resulting from the conversion to either the MRI apparatus 100 or the image storing apparatus 200. Further, the I/F circuitry 310 outputs image data received from either the MRI apparatus 100 or the image storing apparatus 200, to the processing circuitry 350.

The storage circuitry 320 is configured to store therein various types of data. For example, the storage circuitry 320 is realized with a semiconductor memory element such as a Random Access Memory (RAM) or a flash memory, a hard disk, an optical disk, or the like. For example, the storage circuitry 320 is connected to the processing circuitry 350 and stores therein image data input thereto or outputs any of the image data stored therein to the processing circuitry 350, according to an instruction sent thereto from the processing circuitry 350.

The input circuitry 330 is configured to receive input operations of various types of instructions and various types of information from the operator. For example, the input circuitry 330 is realized with a trackball, a switch button, a mouse, a keyboard, a touch panel, and/or the like. For example, the input circuitry 330 is connected to the processing circuitry 350, converts each of the input operations received from the operator into an electric signal, and outputs the electric signal to the processing circuitry 350.

The display 340 is configured to display various types of information and various types of images. For example, the display 340 is realized with a liquid crystal monitor, a Cathode Ray Tube (CRT) monitor, a touch panel, or the like. For example, the display 340 is connected to the processing circuitry 350 and displays images in various formats on the basis of image data output thereto from the processing circuitry 350.

The processing circuitry 350 is configured to control constituent elements of the image processing apparatus 300 according to an input operation output thereto from the input circuitry 330. For example, the processing circuitry 350 may be realized with a processor. For example, the processing circuitry 350 inputs the image data output from the I/F circuitry 310 to the storage circuitry 320. Further, the processing circuitry 350 outputs the image data output from the storage circuitry 320 to the display 340.

The image processing apparatus 300 according to the first embodiment configured as described above is, for example, operated by a medical doctor and used for diagnosing dementia or the like in the brain. Examples of dementia include Alzheimer-type dementia and vascular dementia. It is known that Alzheimer-type dementia prominently exhibits atrophy of cerebral tissues and that vascular dementia prominently exhibits micro bleeds (MBs), in particular.

Further, it has been reported that there is also mixed-type dementia that prominently exhibits both atrophy of cerebral tissues and MBs.

For example, when making a diagnosis by using an MRI apparatus, to diagnose Alzheimer-type dementia, the volume of the cortex is measured by using a T1-weighted image. In contrast, to diagnose vascular dementia, parts having low signals and parts regarded as significantly isolated points in phase shifts are observed by using a T2*-weighted image, a phase image, or a phase-weighted image of an amplitude image, so as to diagnose MBs or calcification.

In this regard, it has been reported that 35% to 85% of vascular dementia exhibits MBs, and it has also been pointed out that it may be possible to predict progress before an onset of vascular dementia by diagnosing MBs. However, for example, it causes medical doctors a lot of trouble to observe MBs with respect to three-dimensional image data acquired by an MRI apparatus in units of slices or in units of projection images obtained by performing a projecting process by implementing a minimum Intensity Projection (mIP) method on slabs having a predetermined thickness. Further, when MBs are present at a boundary between the slabs used in the mIP method or when the slabs are duplicated, there may be situations where it is not possible to properly count the quantity of MBs.

Further, for example, another method has been proposed by which MBs are analyzed by using Susceptibility Weighted Imaging (SWI). However, according to this method, because the quantity of MBs is counted and organized into a table for each of the functional regions of the brain, using this method as a routine requires a lot of trouble. In addition, because there is no criterion for image diagnosis purposes that defines, for example, which parts are regarded as MBs, it is difficult to use the result as an objective index.

In contrast, for example, it is possible to easily use the projection images obtained by implementing the mIP method; however, because there is no information in the depth direction, it is difficult to understand positions in the projecting direction when the projecting process has been performed on the entire brain. For this reason, when some MBs are present in mutually-different positions in the projecting direction, there is a higher possibility that those MBs may overlap each other in a displayed image. In that situation, some MBs are overlooked, and the quantity of MBs is prone to be underestimated.

Further, another method is also possible by which a volume rendering process is performed after MBs are extracted; however, according to this method, although the recognition in the depth direction is better than that of the mIP method, it is not possible to avoid the situation where MBs overlap between the hemispheres of the brain even if the image is rotated. For these reasons, it is difficult to paste an image onto, for example, something like a sheet of paper (e.g., a medical image interpretation report or a medical record) that takes only still images, while properly preventing MBs from overlapping each other.

To cope with these situations, the image processing apparatus 300 according to the first embodiment is configured to be able to alleviate medical doctors' trouble during the process of diagnosing dementia or the like in the brain that is performed while using medical images.

More specifically, the processing circuitry 350 includes an obtaining function 351, a projecting function 352, and an output function 353. The processing circuitry 350 is an example of the processing circuitry set forth in the claims.

The obtaining function 351 is configured to obtain three-dimensional image data of the brain obtained by performing a magnetic resonance imaging process. More specifically, the obtaining function 351 obtains the three-dimensional image data of the brain from either the MRI apparatus 100 or the image storing apparatus 200 via the network 50. Further, the obtaining function 351 causes the storage circuitry 320 to store therein the obtained image data.

For example, the obtaining function 351 obtains the three-dimensional image data acquired by the MRI apparatus 100 by implementing an imaging method that enhances the contrast of MBs or calcification occurring in the brain. For example, the obtaining function 351 obtains three-dimensional image data of a T2*-weighted image, a phase map, a Quantitative Susceptibility Map (QSM) obtained by calculating magnetic susceptibility from a phase map, a magnetic susceptibility image, or a magnetic susceptibility weighted image, a T2* image, or a R2* image, or the like acquired by using a sequence according to a Gradient Echo (GRE) method. The projecting function 352 is configured to generate a projection image rendering micro bleeds or calcification occurring in the brain, by performing a projecting process on the three-dimensional image data obtained by the obtaining function 351 in such a range that is limited on the basis of the shape of the brain. More specifically, the projecting function 352 reads the three-dimensional image data obtained by the obtaining function 351 from the storage circuitry 320 and performs the projecting process on the read three-dimensional image data. Further, the projecting function 352 causes the storage circuitry 320 to store therein image data of the projection image of the brain generated by the projecting process.

For example, by performing the projecting process on the three-dimensional image data, the projecting function 352 generates the projection image rendering the MBs or the calcification occurring in the brain. For example, by performing the projecting process on the three-dimensional image data of a T2*-weighted image, a phase map, a QSM, or the like, it is possible to obtain the projection image rendering the MBs or the calcification. For example, the projecting function 352 generates the projection image of the brain by performing the projecting process implementing the mIP method on the three-dimensional image data.

In this situation, for example, the projecting function 352 performs the projecting process on the three-dimensional image data in the predetermined range limited on the basis of the shape of the brain. For example, the projecting function 352 performs the projecting process by using a range from the surface of the brain (hereinafter, "brain surface") to a predetermined depth as the predetermined range.

Figure 2:
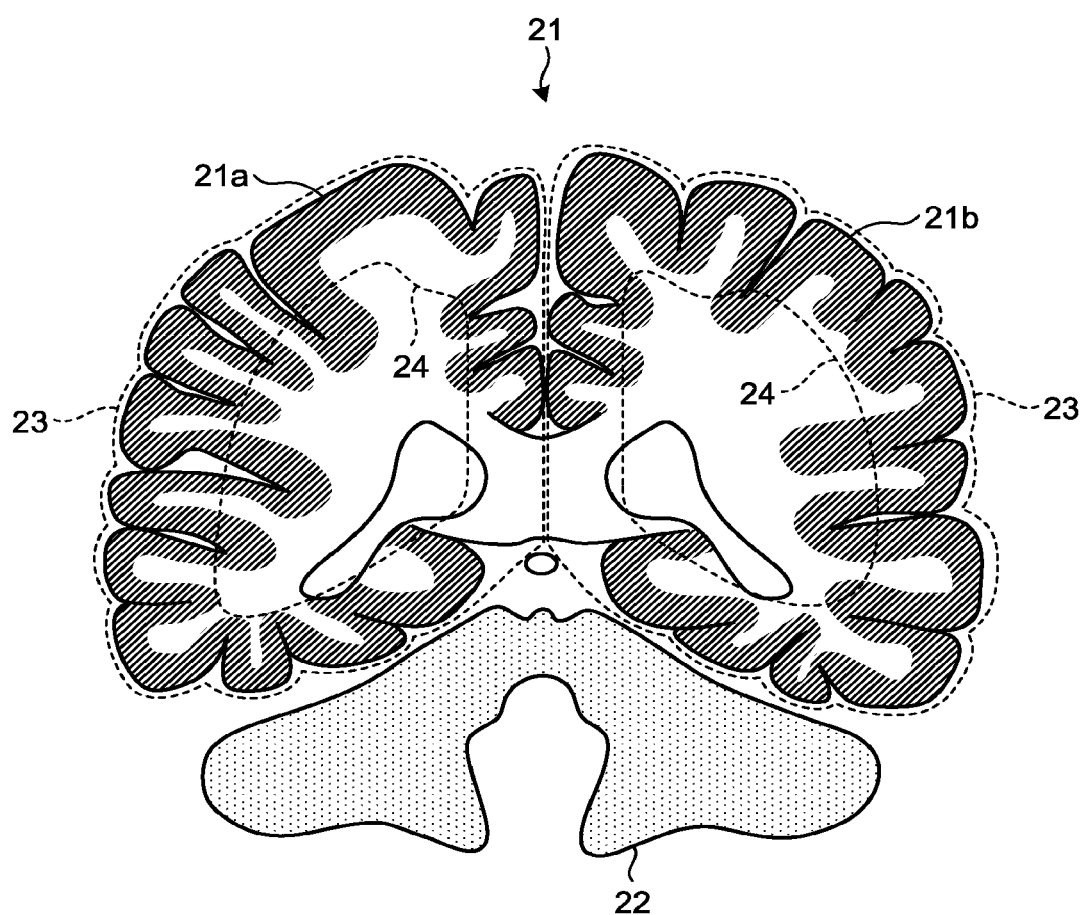
FIG. 2 is a drawing of an example of a projecting process performed by a projecting function according to the first embodiment.

FIG. 2 is a drawing of an example of the projecting process performed by the projecting function 352 according to the first embodiment. FIG. 2 illustrates a cross-sectional view of the brain taken along a coronal cross-sectional plane. In FIG. 2, the hatching indicates the cortex (gray matter), whereas the white area inside the cortex indicates white matter. Further, the dotted shade indicates the cerebellum.

For example, as illustrated in FIG. 2, in the three-dimensional image data, the projecting function 352 deletes the sites on the outside of the brain such as the scalp, the cranium, and the like, and further separates the cerebrum 21 and the cerebellum 22 from each other, before dividing the cerebrum 21 into the right hemisphere 21a and the left hemisphere 21b.

After that, the projecting function 352 sets the range from the brain surface to the predetermined depth (the range between the broken line 23 and the broken line 24 in FIG. 2) in the right hemisphere 21a and in the left hemisphere 21b. For example, the range from the brain surface to the predetermined depth may be defined as a range from the exterior surface of the brain excluding the surface inside the sulci (i.e., a curved plane as indicated with the broken line 23 in FIG. 2 drawn along the exterior surface of the gyri) to the predetermined depth. In another example, the range from the brain surface to the predetermined range may be defined as a range from the exterior surface of the brain including the surface inside the sulci to the predetermined depth. The predetermined depth in this situation may be a constant depth or may be different in different positions of the brain. Further, when the predetermined depth is constant, the range that is set includes some white matter because the thickness of the cortex is not constant. However, it is desirable to set the range so as to include much of the cortex part, while excluding as much of the white matter part as possible.

After that, the projecting function 352 performs the projecting process that implements the mIP method in the set range. In that situation, for example, the projecting function 352 performs projecting processes by using one or more projecting directions obtained by viewing the brain surface from one or more directions, without changing the shape of the brain. More specifically, for example, the projecting function 352 performs the projecting processes on the right hemisphere 21a and on the left hemisphere 21b, by using the directions obtained by viewing each of the brain hemispheres from the lateral surface and the medial surface. Further, for example, the projecting function 352 performs projecting processes by using the directions obtained by viewing both the right hemisphere 21a and the left hemisphere 21b together, from the top surface and from the bottom surface. Further, for example, the projecting function 352 may also perform projecting processes by using directions obtained by viewing both the right hemisphere 21a and the left hemisphere 21b together, from the front surface and from the rear surface.

The example is explained above in which the projecting processes are performed in the range from the brain surface to the predetermined depth; however, possible methods for performing the projecting processes are not limited to this example. For instance, the projecting function 352 may extract a cortex region by performing a segmentation process on the three-dimensional image data and further perform a projecting process on the extracted cortex region. In that situation, the projecting function 352 detects the cortex region on the basis of a predetermined threshold value that is set in advance as a threshold for signal values for the purpose of extracting the cortex.

Further, the example is explained above in which the projecting processes are performed on the cortex region in the three-dimensional image data; however, possible methods for performing the projecting processes are not limited to this example. Generally speaking, the cortex (a set of neurons that is present in the space between the brain surface and a certain depth) can be divided into regions according to functions of the brain, and it is known that the part beneath the cortex and the deeper part are primarily white matter representing nerve fibers. In this situation, regarding lesions in the white matter also, disorders occurring in a part corresponding to a liaison between a corresponding section of the cortex and a motor nerve or a sensory nerve are considered to be related to the corresponding one of the functions of the brain. For this reason, for example, the projecting function 352 may perform a projecting process on a white matter part. Further, the projecting function 352 may perform projecting processes at stages by, for example, performing, at first, a projecting process on the cortex part and subsequently performing a projecting process on a white matter part as necessary.

The output function 353 outputs the projection images generated by the projecting function 352 to the display 340. More specifically, the output function 353 reads, from the storage circuitry 320, the image data of the projection images generated by the projecting function 352 and further outputs the read image data to the display 340.

Figure 3:
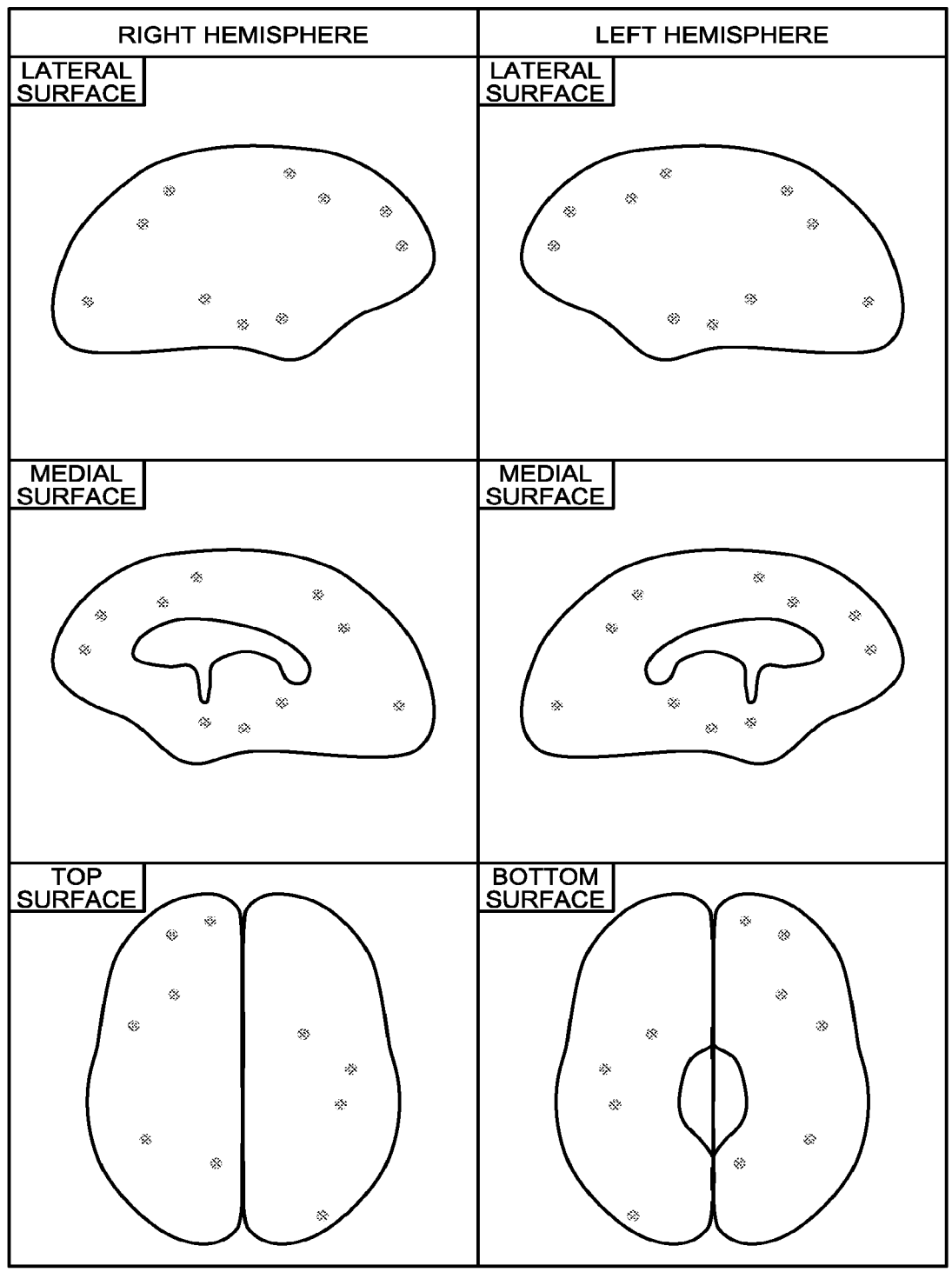
FIG. 3 is a drawing of examples of projection images output by an output function according to the first embodiment.

FIG. 3 is a drawing of examples of the projection images output by the output function 353 according to the first embodiment. For example, as illustrated in FIG. 3, the output function 353 outputs projection images viewed from the lateral surface and from the medial surface with respect to each of the right and the left hemispheres. Further, the output function 353 outputs projection images obtained by viewing both the right hemisphere 21a and the left hemisphere 21b together from the top surface and from the bottom surface. Also, for example, the output function 353 may further output projection images obtained viewing both the right hemisphere 21a and the left hemisphere 21b together, from the front surface and from the rear surface. In FIG. 3, the regions indicated with dots in the images of the brain represent regions of MBs or calcification sites.

The output function 353 may output the projection images together with one or more images of the brain surface.

Figure 4:
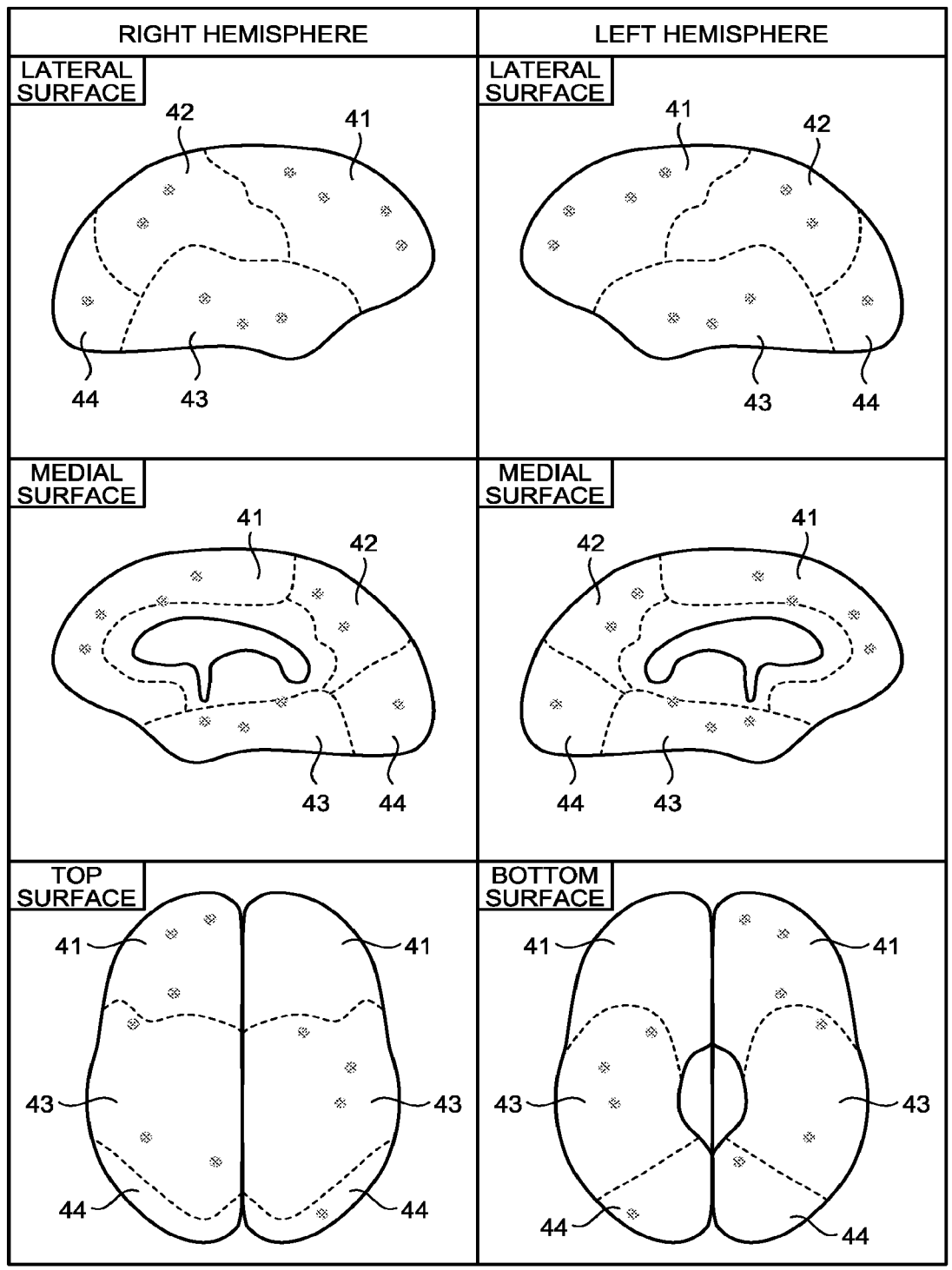
FIG. 4 is a drawing of other examples of projection images output by the output function according to the first embodiment.

FIG. 4 is a drawing of other examples of the projection images output by the output function 353 according to the first embodiment. For example, as illustrated in FIG. 4, the output function 353 outputs the projection images so as to be superimposed on images of the brain surface rendering the frontal lobe 41, the parietal lobe 42, the temporal lobe 43, and the occipital lobe 44, which are sectioned by a broader classification according to the functional regions of the brain. The images of the brain surface used in this situation do not necessarily have to render the frontal lobe, the parietal lobe, the temporal lobe, and the occipital lobe. For example, the images of the brain surface may render functional regions sectioned according to a Brodmann's brain map which further divides the region of the brain according to the functions thereof with a finer classification.

In this situation, for example, the output function 353 identifies the position of each of the regions in the projection images, by using a template image in which the sections according to the brain functions are indicated in a standard shape of the brain. For example, the output function 353 identifies the position of each of the regions in the projection images by matching the template image, while varying the shape thereof, with an image (e.g., a T1 W image) that renders the same patient as in the projection images to be displayed and that renders the shape of the brain relatively clearly.

Further, for example, the output function 353 may output the projection images so as to be superimposed onto a predetermined type of parameter images related to the same brain. In this situation, for example, the parameter images may be a Cerebral Blood Flow (CBF) images indicating blood flows in the brain or may be images mapping the thickness of the cortex, T1 values, T2 values, Proton Density (PD) values, Apparent Diffusion Coefficient (ADC) values, Fractional Anisotropy (FA) values, and/or the like. For example, images mapping CBF have, generally speaking, a slice thickness of 2 to 3 cm at most in many situations, and it is considered that the possibility of having a plurality of MBs or calcification sites overlapping each other is low, even when the projecting process is performed by using the same thickness. The parameter images used in this situation are, for example, obtained by the obtaining function 351 in advance and stored in the storage circuitry 320.

Further, for example, the output function 353 may output the projection images so as to be superimposed on images acquired by an image diagnosis apparatus other than the MRI apparatus 100. In this situation, the other image diagnosis apparatus may be, for example, an X-ray CT apparatus, an ultrasound diagnosis apparatus, a PET apparatus, or the like. The images acquired by the other image diagnosis apparatus are, for example, obtained by the obtaining function 351 in advance and stored into the storage circuitry 320.

Processing functions of the processing circuitry 350 have thus been explained. In the present example, for example, the processing functions described above are stored in the storage circuitry 320 in the form of a computer-executable program. The processing circuitry 350 realizes the processing functions corresponding to the computer programs (hereinafter, "programs") by reading the programs from the storage circuitry 320 and executing the read programs. In other words, the processing circuitry 350 that has read the programs has the processing functions illustrated in FIG. 1.

Further, FIG. 1 illustrates the example in which the single processing circuit (the processing circuitry 350) realizes the processing functions such as the obtaining function 351, the projecting function 352, and the output function 353; however, possible embodiments are not limited to this example. For instance, the processing circuitry 350 may be structured by combining a plurality of independent processors together, so that the processing functions are realized as a result of the processors executing the programs. Further, the processing functions included in the processing circuitry 350 may be realized as being distributed or integrated together into single processing circuitry or a plurality of processing circuitries, as appropriate.

Figure 5:
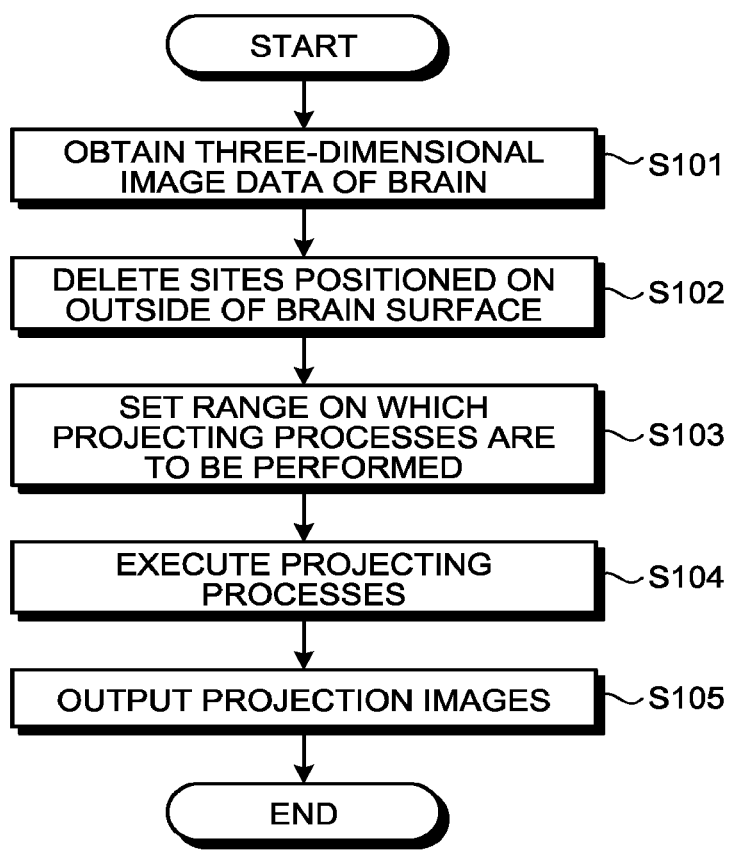
FIG. 5 is a flowchart illustrating a processing procedure according to an image processing method implemented by the image processing apparatus according to the first embodiment.

FIG. 5 is a flowchart illustrating a processing procedure according to an image processing method implemented by the image processing apparatus 300 according to the first embodiment.

For example, as illustrated in FIG. 5, in the image processing apparatus 300, the obtaining function 351 obtains the three-dimensional image data of the brain from either the MRI apparatus 100 or the image storing apparatus 200 (step S101). The process at step S101 is realized as a result of, for example, the processing circuitry 350 invoking, from the storage circuitry 320, and executing a predetermined program corresponding to the obtaining function 351.

Subsequently, the projecting function 352 deletes the sites (e.g., the scalp, the cranium, and the like) positioned on the outside of the brain from the three-dimensional image data (step S102). After that, the projecting function 352 sets a range on which the projecting processes are to be performed (step S103) and further executes the projecting processes in the set range (step S104). The processes at steps S102 through S104 are realized as a result of, for example, the processing circuitry 350 invoking, from the storage circuitry 320, and executing a predetermined program corresponding to the projecting function 352.

Subsequently, the output function 353 outputs the projection images generated by the projecting function 352 to the display 340 (step S105). The process at step S105 is realized as a result of, for example, the processing circuitry 350 invoking, from the storage circuitry 320, and executing a predetermined program corresponding to the output function 353.

As explained above, in the first embodiment, the projection images rendering the MBs or the calcification occurring in the brain are obtained, by performing the projecting processes on the three-dimensional image data of the brain. In other words, as long as it is possible to extract the brain surface, it is possible to display the MBs or the calcification without the need to perform the process of extracting the cortex or the white matter of the brain tissues or lesions such as MBs or calcification.

Further, in the first embodiment, because the projection images are output together with the images of the brain surface, it is possible to easily identify the positions of the lesions occurring in the brain.

Further, in the first embodiment, the projecting processes are performed in the range that is limited on the basis of the shape of the brain within the three-dimensional image data, instead of being performed on the entirety of the brain. Accordingly, it is possible to prevent the situation where a plurality of MBs or calcification sites overlap one another in the projection images.

Further, in the first embodiment, the projecting processes are performed by using the projecting directions obtained by viewing the brain surface from the one or more directions. Accordingly, it is possible to easily observe the MBs and the calcification sites in the projection images, which are still images, without the need to observe the MBs or the calcification sites in a moving picture in which the projecting directions are rotated. Further, it is possible to easily use the projection images, which are still images, in a medical image interpretation report or a medical record.

Further, in the first embodiment, the projection images are output as being superimposed on the predetermined type of parameter images. Accordingly, the viewer is able to easily understand the relationship between various types of parameters in a qualitative or quantitative manner, and it is therefore possible to improve the level of performance in the diagnosis procedure.

As explained above, according to the first embodiment, it is possible to alleviate medical doctors' trouble during the process of diagnosing dementia or the like in the brain that is performed while using the medical images.

First Modification Example

In the first embodiment above, the example is explained in which the projecting function 352 performs the projecting processes in the projecting directions obtained by viewing the brain surface from the one or more directions; however, possible methods for performing the projecting processes are not limited to this example.

For example, the projecting function 352 may divide the region of the brain in the three-dimensional image data into a plurality of regions and perform a projecting process on each of the regions resulting from the division.

Figure 6:
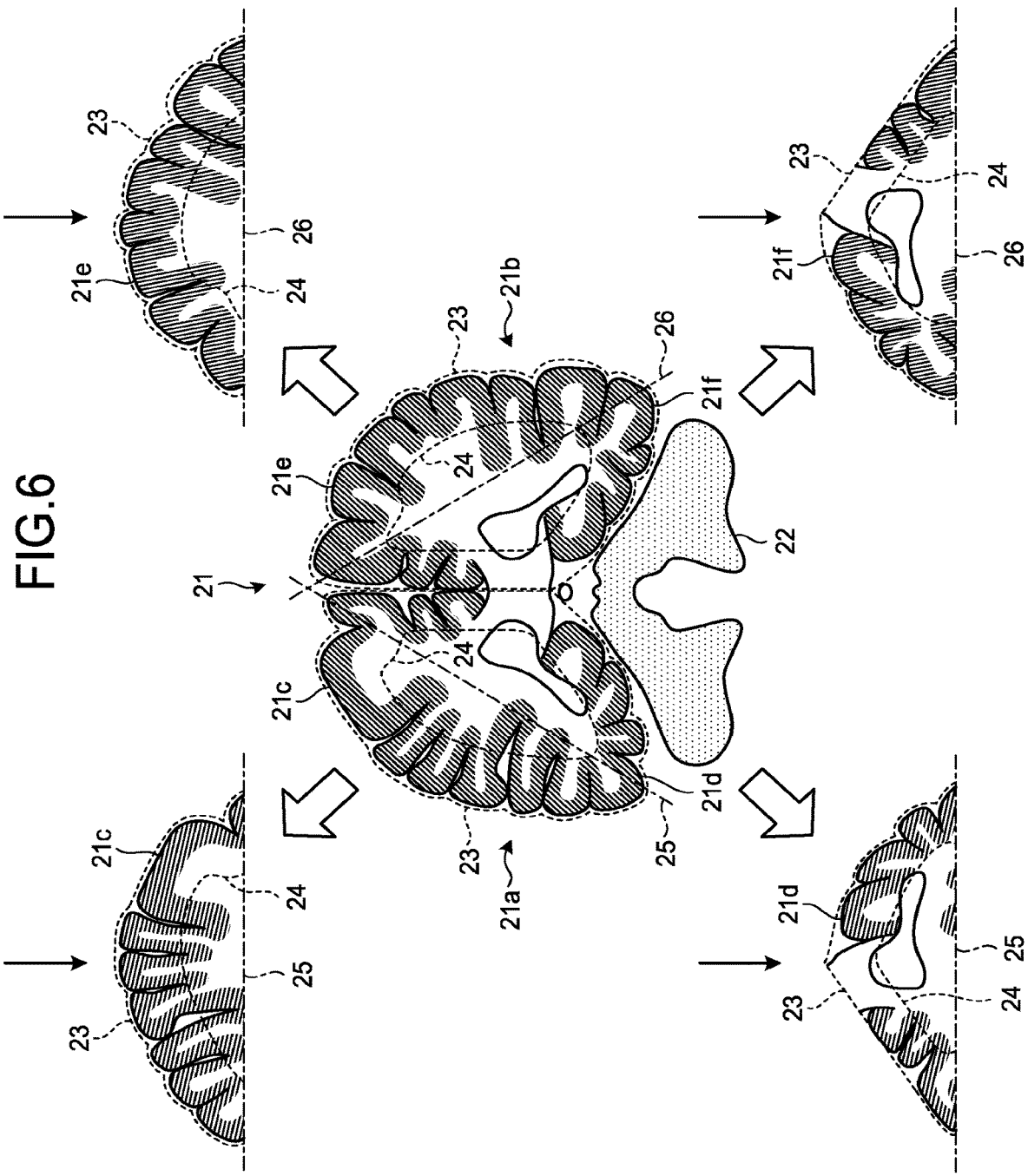
FIG. 6 is a drawing of an example of a projecting process performed by a projecting function according to the first modification example.

FIG. 6 is a drawing of an example of the projecting process performed by the projecting function 352 according to the first modification example. FIG. 6 illustrates a cross-sectional view of the brain taken along a coronal cross-sectional plane, similarly to the example illustrated in FIG. 2. In FIG. 6, the hatching indicates the cortex (gray matter), whereas the white area inside the cortex indicates white matter. Further, the dotted shade indicates the cerebellum.

Further, as illustrated in FIG. 6, in the three-dimensional image data, the projecting function 352 deletes the sites on the outside of the brain such as the scalp, the cranium, and the like, and further separates the cerebrum 21 and the cerebellum 22 from each other, before dividing the cerebrum 21 into the right hemisphere 21a and the left hemisphere 21b. After that, the projecting function 352 sets the range from the brain surface to the predetermined depth (the range between the broken line 23 and the broken line 24 in FIG. 6) in the right hemisphere 21a and in the left hemisphere 21b. These processes are the same as those in the example illustrated in FIG. 2.

After that, in a first modification example, as illustrated in FIG. 6 for instance, the projecting function 352 divides the right hemisphere 21a into a region 21c including the lateral surface and the top surface and another region 21d including the medial surface and the bottom surface, with a projection plane 25 passing through the right hemisphere 21a. Further, the projecting function 352 divides the left hemisphere 21b into a region 21e including the lateral surface and the top surface and another region 21f including the medial surface and the bottom surface, with a projection plane 26 passing through the left hemisphere 21b. In this situation, for example, the projection planes 25 and 26 are each a plane perpendicular to the coronal cross-sectional plane.

After that, the projecting function 352 performs projecting processes implementing the mIP method in the set range. In this situation, for example, the projecting function 352 performs the projecting processes by using projecting directions (the directions indicated by the solid arrows in FIG. 6) perpendicular to the projection planes without changing the shape of the brain, with respect to each of the divided regions. As a result, four projection images are obtained, namely, a projection image including the lateral surface and the top surface of the right hemisphere 21a, a projection image including the medial surface and the bottom surface of the right hemisphere 21a, a projection image including the lateral surface and the top surface of the left hemisphere 21b, and a projection image including the medial surface and the bottom surface of the left hemisphere 21b.

As explained above, by performing the projecting processes by dividing the region of the brain into the four regions, it is possible to observe the entire brain by using a smaller number of projection images than in the situation where the projecting processes are performed from the eight directions (the directions obtained by viewing the brain from the lateral surface and the medial surface of the right hemisphere, the lateral surface and the medial surface of the left hemisphere, the top surface, and the bottom surface) as described in the first embodiment.

Generally speaking, because the brain is oblong in the front-and-back direction, it is preferable to divide the region of the brain by using a plane perpendicular to the coronal cross-sectional plane; however, possible methods for dividing the region of the brain are not limited to this example. For instance, the projecting function 352 may cause the display 340 to display a sagittal cross-sectional image of the brain and receive, from the operator, an operation to set the position of a cross-sectional plane used for dividing the brain region into sections within the displayed sagittal cross-sectional image.

Further, the units into which the region of the brain is divided are not limited to those described in the above example. For instance, the projecting function 352 may divide the region of the brain into a plurality of regions sectioned according to the functions thereof.

For example, the projecting function 352 divides the region of the brain into a plurality of regions including the frontal lobe, the parietal lobe, the temporal lobe, and the occipital lobe. Alternatively, for example, the projecting function 352 may divide the region of the brain into a plurality of regions sectioned according to a Brodmann's brain map. In another example, the projecting function 352 may divide the region of the brain into a plurality of regions sectioned in correspondence with blood-vessel dominant regions.

Second Modification Example

In the first embodiment described above, the example is explained in which the projecting function 352 performs the projecting processes without changing the shape of the brain; however, possible methods for performing the projecting processes are not limited to this example.

For instance, the projecting function 352 may perform the projecting processes after changing the shape of the brain. For example, the projecting function 352 may perform the projecting processes after converting the three-dimensional image data in such a manner that surface of the brain is aligned on a flat plane.

Figure 7:
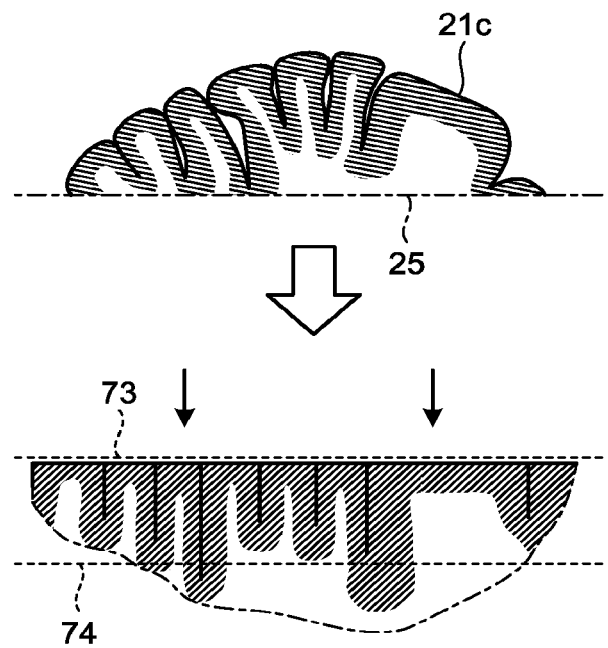
FIG. 7 is a drawing of an example of a projecting process performed by a projecting function according to a second modification example.

FIG. 7 is a drawing of an example of a projecting process performed by the projecting function 352 according to a second modification example. For example, similarly to the example illustrated in FIG. 6, the projecting function 352 divides the right hemisphere into a region including the lateral surface and the top surface and another region including the medial surface and the bottom surface and divides the left hemisphere into a region including the lateral surface and the top surface and another region including the medial surface and the bottom surface. In the following sections, from among the four regions resulting from the division, an example with the region 21c including the lateral surface and the top surface of the right hemisphere 21a will be explained; however, the same process is also performed on each of the other regions.

For example, as illustrated in FIG. 7, the projecting function 352 converts the three-dimensional image data of the brain by stretching out the region on the inside of the brain in such a manner that the brain surface (indicated with the broken line 73 in FIG. 7) is aligned on a flat plane. After that, the projecting function 352 sets a range from the brain surface to a predetermined depth (the range between the broken line 73 and the broken line 74 in FIG. 7). Further, the projecting function 352 performs projecting processes implementing the mIP method in the set range.

As a result, it is possible to obtain a projection image in which the lateral surface and the top surface of the right hemisphere 21a are stretched out so that the brain surface is flat. Further, by performing the same process, it is also possible to obtain a projection image in which the medial surface and the bottom surface of the right hemisphere 21a are stretched out so that the brain surface is flat, another projection image in which the lateral surface and the top surface of the left hemisphere 21b are stretched out so that the brain surface is flat, and yet another projection image in which the medial surface and the bottom surface of the left hemisphere 21b are stretched out so that the brain surface is flat.

Further, for example, the projecting function 352 may perform projecting processes by extracting a cortex part of the brain in the three-dimensional image data and subsequently converting the three-dimensional image data in such a manner that the surface of the extracted cortex part is aligned on a flat plane.

Figure 8:
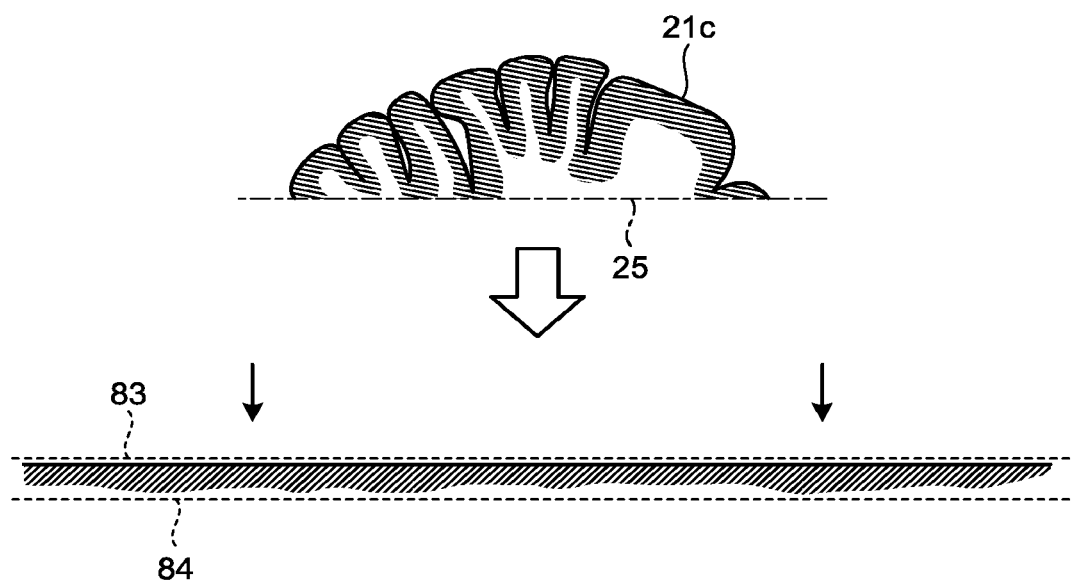
FIG. 8 is a drawing of another example of the projecting process performed by the projecting function according to the second modification example.

FIG. 8 is a drawing of another example of the projecting process performed by the projecting function 352 according to the second modification example. For example, similarly to the example illustrated in FIG. 6, the projecting function 352 divides the right hemisphere into a region including the lateral surface and the top surface and another region including the medial surface and the bottom surface and divides the left hemisphere into a region including the lateral surface and the top surface and another region including the medial surface and the bottom surface. In the following sections, from among the four regions resulting from the division, an example with the region 21c including the lateral surface and the top surface of the right hemisphere 21a will be explained; however, the same process is also performed on each of the other regions.

For example, as illustrated in FIG. 8, the projecting function 352 converts the three-dimensional image data of the brain by extracting a cortex region through a segmentation process performed on the three-dimensional image data and subsequently stretching out the extracted cortex region so that the surface (indicated with the broken line 83 in FIG. 8) is aligned on a flat plane. After that, the projecting function 352 sets a range from the brain surface to a predetermined depth (the range between the broken line 83 and the broken line 84 in FIG. 8). In this situation, the predetermined depth is set so as to define the range including the extracted cortex part.

Further, the projecting function 352 performs projecting processes implementing the mIP method in the set range. As a result, it is possible to obtain a projection image in which the lateral surface and the top surface of the right hemisphere 21a are stretched out so that the surface of the cortex part is flat. Further, by performing the same process, it is also possible to obtain a projection image in which the medial surface and the bottom surface of the right hemisphere 21a are stretched out so that the surface of the cortex part is flat, another projection image in which the lateral surface and the top surface of the left hemisphere 21b are stretched out so that the surface of the cortex part is flat, and yet another projection image in which the medial surface and the bottom surface of the left hemisphere 21b are stretched out so that the surface of the cortex part is flat.

The first and the second modification examples have thus been explained. According to these modification examples, because the projecting processes are performed after the region of the brain is divided into the sections, there is no possibility that a single MB or a single calcification site is displayed in duplicate in two or more projection images. Thus, it is possible to accurately count the quantity of the MBs or the calcification sites in the diagnosis procedure.

Further, in the embodiments and the modification examples described above, the example is explained in which the projecting function 352 performs the projecting processes by implementing the mIP method; however, possible methods for performing the projecting processes are not limited to this example. For instance, an average intensity projection method, a Maximum Intensity Projection (MIP) method, or the like may be used.

For example, the projecting function 352 may vary the method for performing the projecting processes depending on the type of images used in a diagnosis procedure. More specifically, when a T2*-weighted image or a phase map is used, for example, because the signal values of MBs and calcification sites are smaller than the signal values in the surrounding areas thereof, the projecting function 352 uses the mIP method for the projecting processes. In contrast, when a QSM is used, for example, because the signal values of MBs and calcification sites are larger than the signal values of the surrounding areas thereof, the projecting function 352 uses the MIP method. Alternatively, the projecting function 352 may use an average intensity projection method in common to a plurality of types of images.

Third Modification Example

In the first embodiment described above, the examples are explained in which the output function 353 outputs the projection images together with the images of the brain surface and the output function 353 outputs the projection images as being superimposed on the predetermined type of parameter images related to the same brain; however, possible methods for outputting the projection images are not limited to these examples.

For instance, the output function 353 may output, as being superimposed on the projection images, graphic elements indicating a plurality of regions obtained by dividing the region of the brain into sections according to the functions thereof as Regions of Interest (ROIs). In this situation, the plurality of regions may be a plurality of regions including the frontal lobe, the parietal lobe, the temporal lobe, and the occipital lobe. Alternatively, the plurality of regions may be a plurality of regions sectioned according to a Brodmann's brain map or may be a plurality of regions sectioned in correspondence with blood-vessel dominant regions. In this situation also, the output function 353 identifies the position of each of the regions in the projection images by using, for example, the template image of the brain as explained above.

Figure 9:
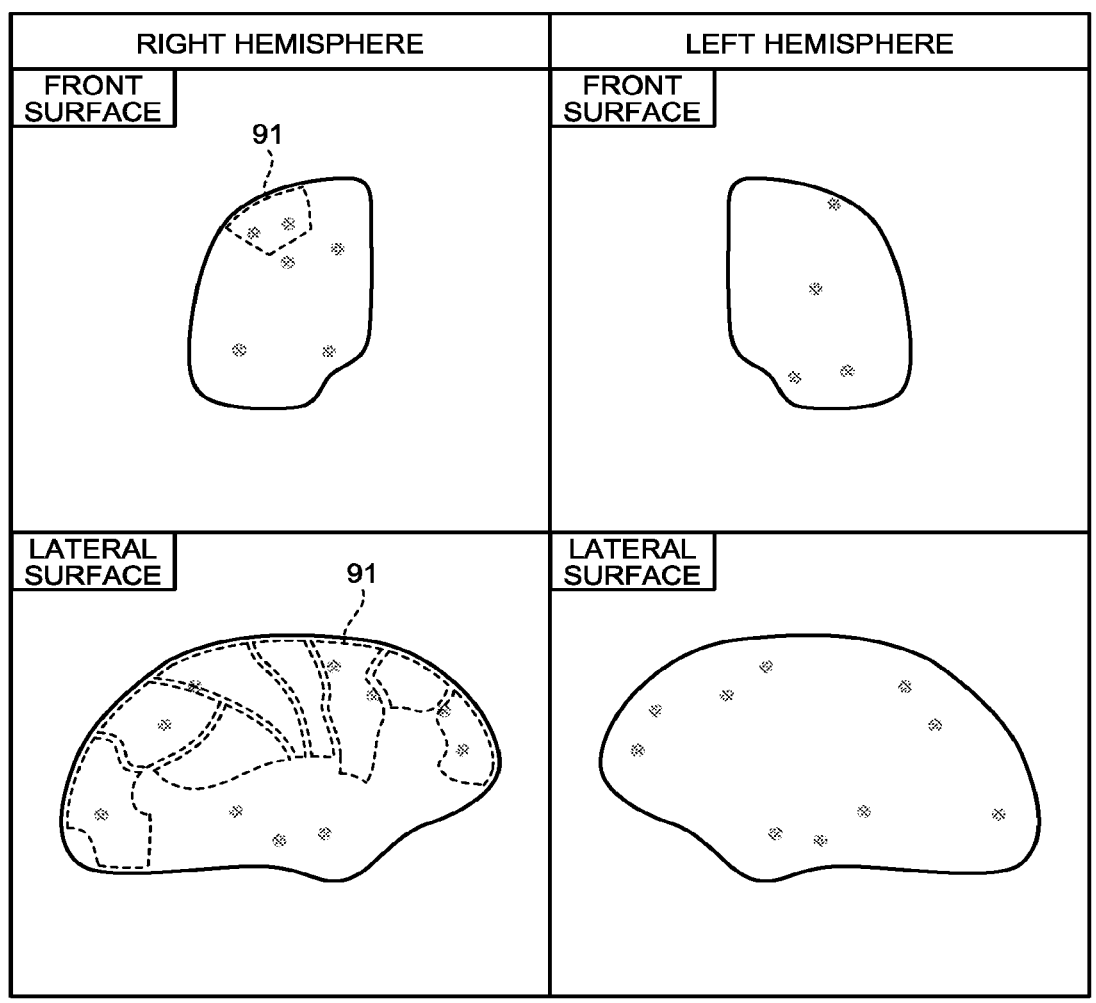
FIG. 9 is a drawing of examples of projection images output by an output function according to a third modification example.

FIG. 9 is a drawing of examples of the projection images output by the output function 353 according to a third modification example. FIG. 9 illustrates an example in which a projection image from the front surface and a projection image from the lateral surface are displayed for each of the right and the left hemispheres. For example, as illustrated in FIG. 9, the output function 353 outputs graphic elements (indicated with the broken lines in FIG. 9) indicating the outlines of the regions so as to be superimposed on the projection images. In this situation, for example, the output function 353 may display the graphic elements indicating only the outlines of the regions as the graphic elements 91 or may display the graphic elements that are in mutually-different colors or that have mutually-different patterns in correspondence with the regions in a semi-transparent manner.

FIG. 9 illustrates the example in which the graphic elements are displayed only in the projection images of the right hemisphere; however, the output function 353 may display the graphic element in all or a part of the projection images. For example, the output function 353 may display the graphic element in one or more projection images designated by the operator via the input circuitry 330, from among the plurality of projection images displayed.

As explained above, according to the third modification example, the graphic elements indicating the plurality of regions obtained by dividing the region of the brain into the sections according to the functions thereof are displayed as being superimposed on the projection images. Accordingly, the operator is able to easily understand the positional relationship between the regions of the brain sectioned according to the functions thereof and the MBs or the calcification sites occurring in the brain.

Fourth Modification Example

In the first embodiment described above, the example is explained in which the output function 353 outputs the projection images; however, possible methods for outputting the information related to the MBs or the calcification are not limited to this example.

For instance, the output function 353 may further output a measured result related to the MBs or the calcification, on the basis of the three-dimensional image data of the brain.

For example, by performing projecting processes on the three-dimensional image data of the brain from a plurality of mutually-different directions, the projecting function 352 generates a plurality of projection images corresponding to the directions. Further, the output function 353 outputs a measured result related an MB or a calcification site that is present in a position designated within the plurality of projection images.

Figures 10, 11:
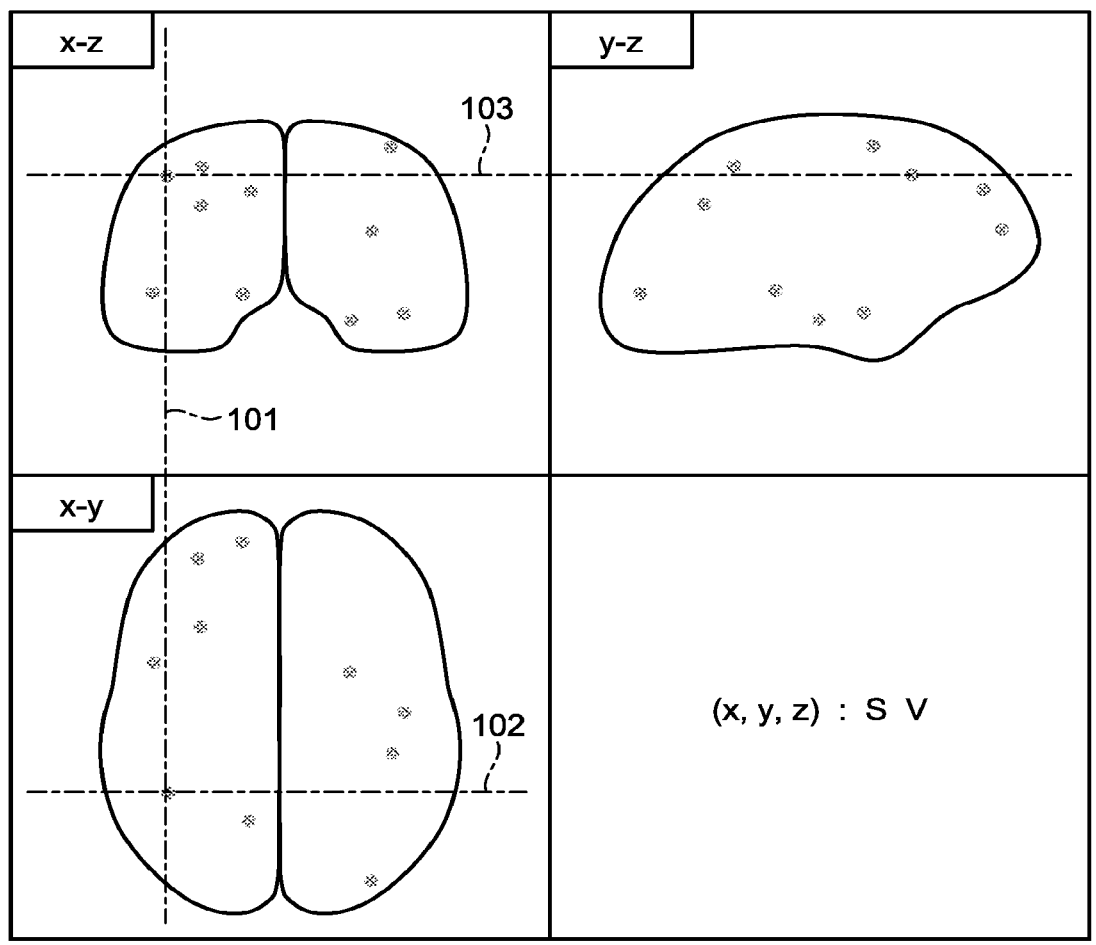
FIG. 10 is a drawing of an example of a measured result output by an output function according to a fourth modification example.
FIG. 11 is a drawing of another example of a measured result output by the output function according to the fourth modification example.

FIG. 10 is a drawing of an example of the measured result output by the output function 353 according to a fourth modification example. For instance, as illustrated in FIG. 10, the output function 353 outputs, to the display 340, three projection images obtained by performing projecting processes from the directions of the x-axis, the y-axis, and the z-axes that are orthogonal to one another. In other words, the output function 353 outputs a projection image obtained by projecting the brain in the x-axis direction (a projection image using the y-z plane as the projection plane thereof), a projection image obtained by projecting the brain in the y-axis direction (a projection image using the x-z plane as the projection plane thereof), and a projection image obtained by projecting the brain in the z-axis direction (a projection image using the x-y plane as the projection plane thereof).

Further, the output function 353 outputs a graphic element 101 indicating positions in the x-axis direction, a graphic element 102 indicating positions in the y-axis direction, and a graphic element 103 indicating positions in the z-axis direction, in the three projection images. An intersection point of the graphic elements represents a position in the three-dimensional space expressed by the x-axis, the y-axis, and the z-axis and can be expressed with coordinates (x,y,z). Accordingly, the operator is able to designate any arbitrary position in the three-dimensional space by moving the graphic elements as appropriate along the axial directions via the input circuitry 330.

Further, on the basis of the three-dimensional image data from which the projection images were generated, the output function 353 detects the region of an MB or a calcification site in the position designated by the operator and further measures the signal intensity and the volume of the detected region. For example, as the signal intensity of the detected region, the output function 353 measures an average value or a maximum value of the signal intensities of the voxels included in the region. In this situation, for example, the output function 353 detects the MB or the calcification site by detecting a region having a shape close to a sphere or a region isolated from the surrounding thereof. As a result, for example, it is possible to exclude blood vessels because oblong regions and continuous regions are not detected.

After that, the output function 353 displays the signal intensity and the volume that were measured together with the projection images. For example, as illustrated in FIG. 10, the output function 353 displays the position (x,y,z) designated by the operator together with a measured signal intensity S and a measured volume V expressed with numerical values. After that, when the operator designates a new position in the projection images by moving the graphic elements 101 to 103, the output function 353 again measures the signal intensity and the volume of an MB or a calcification site on the basis of the designated position and updates the displays of the signal intensity and the volume in a real-time manner.

Generally speaking, because projection images obtained by performing projecting processes such as those implementing the mIP method lose the information in the depth direction, it would be difficult to understand positions in the projecting direction. In contrast, with the above arrangements, by designating a position in the plurality of projection images corresponding to the mutually-different directions, the operator is able to easily identify the position of an MB or a calcification site. Consequently, it is easier to perform the measuring process related to MBs or calcification sites.

Alternatively, for example, the output function 353 may output a measured result related to MBs or calcification sites by using a list format.

FIG. 11 is a drawing of another example of the measured result output by the output function 353 according to the fourth modification example. For instance, as illustrated in FIG. 11, the output function 353 displays, together with the projection images, a list 111 indicating the quantity and the volume of the detected MBs or calcification regions, for each of the plurality of regions into which the region of the brain is divided according to the functions thereof. In FIG. 11, the characters "A", "B", and "C" indicate the regions sectioned according to the functions thereof. Further, the numerical values "8", "10", and "12" indicate the quantity of MBs or calcification regions in the respective regions. Further, the numerical values "10/90", "15/100", and "20/120" indicate "the volume of the MBs or the calcification regions"/"the volume of the region sectioned according to the function thereof".

In this manner, when the measured result is output for each of the regions sectioned according to the functions of the brain, the operator is able to easily understand the relationship between the regions sectioned according to the brain functions and the MBs or the calcification sites.

As explained above, according to the fourth embodiment, the measured results related to the MBs or the calcification sites are output on the basis of the three-dimensional image data of the brain. It is therefore possible to present the operator with the quantitative indexes to be used in the process of diagnosing the MBs or the calcification.

The example in which the measured results are output as the numerical values is explained above; however, possible methods for outputting the measured results are not limited to this example. For instance, the output function 353 may output the numerical values representing the measured results by using a color-coded scheme, so that the viewer is able to recognize, by color, the numerical values representing the measured results. In that situation, for example, the output function 353 displays the regions sectioned according to the functions thereof so as to be superimposed on the projection images and further displays each of the regions in a specific color in a semi-transparent manner in accordance with the measured result of the region.

Further, for example, in addition to outputting the measured results to the display 340, the output function 353 may also store the measured results into a database constructed in the storage circuitry 320. With this arrangement, for example, by referring to measured results accumulated for a certain period of time, the operator is able to analyze a chronological change in the MBs or the calcification sites.

Fifth Modification Example

Further, in the first embodiment and the modification examples described above, the examples are explained in which the projecting function 352 performs the projecting processes by implementing the mIP method, the MIP method, or the average intensity projection method; however, possible methods for performing the projecting processes are not limited to these examples.

For instance, the projecting function 352 may generate a projection image of the brain by performing a volume rendering process on the three-dimensional image data obtained by the obtaining function 351. In this situation, the projection image is a volume rendering image.

For example, the projecting function 352 extracts the regions of MBs or calcification sites included in the three-dimensional image data of the brain by performing a segmentation process and further outputs a volume rendering image of the extracted regions to the display 340. At that time, the projecting function 352 detects the regions of the MBs or the calcification sites, on the basis of a predetermined threshold value that is set in advance as a threshold value for signal values for the purpose of extracting the MBs or the calcification sites. In that situation, for example, when the difference in signal value is small between the regions of the MBs or the calcification sites and the surrounding regions, the projecting function 352 performs the segmentation process by using an enlargement/reduction method or the like.

In another example, the projecting function 352 may further extract a region of a predetermined site included in the three-dimensional image data of the brain by performing a segmentation process and may output a volume rendering image of the extracted region of the site so as to be superimposed on the volume rendering image of the regions of the MBs or the calcification sites. For example, the projecting function 352 may output a volume rendering image of a region of a blood vessel so as to be superimposed on the volume rendering image of the region of the MBs or the calcification sites. In that situation, for example, the projecting function 352 may output the regions of the MBs or the calcification sites and the region of the predetermined site in mutually-different colors.

Further, for example, when the output function 353 performs the measuring process related to MBs or calcification sites, the projecting function 352 extracts the region of the entire brain from the three-dimensional image data by performing a segmentation process. Further, by performing a segmentation process, the output function 353 detects the regions of the MBs or the calcification sites from the region of the entire brain extracted by the projecting function 352 and further measures the quantity, the volume, the signal intensity, and the like with respect to the detected regions.

Alternatively, for example, the projecting function 352 may extract, from the three-dimensional image data, a plurality of regions obtained by dividing the brain into sections according to the functions thereof and may perform a measuring process related to MBs or calcification sites for each of the extracted regions. In this situation, the plurality of regions may be, for example, a plurality of regions including the frontal lobe, the parietal lobe, the temporal lobe, and the occipital lobe. Alternatively, the plurality of regions may be a plurality of regions sectioned according to a Brodmann's brain map or may be a plurality of regions sectioned in correspondence with blood-vessel dominant regions. Also, for example, it is also acceptable to perform a measuring process by dividing the brain into a cortex part and a white matter part.

As additional information, also when the volume rendering process is used, it is possible to use the same method as the method described in the first embodiment and the modification examples, as the method for displaying the volume rendering image and for displaying the measured results of the MBs or the calcification sites.

Further, when the volume rendering process is used, for example, the output function 353 may receive, from the operator, an operation to remove a part of the image of the brain or to open a hole in the image of the brain within the volume rendering image of the brain displayed by the display 340 via the input circuitry 330. In that situation, the output function 353 displays a cross-sectional plane created by the removal or the hole by performing a volume rendering process in accordance with the received operation and further displays regions of MBs or calcification sites on the cross-sectional plane.

As explained above, according to the fifth modification example, because the projection image of the brain is generated by performing the volume rendering process on the three-dimensional image data, it is possible to diagnose the MBs or the calcification, by effectively using the three-dimensional information including the information in the depth direction.

Sixth Modification Example

The first embodiment and some modification examples have thus been explained; however, the range and the set values such as the threshold values used in the processes described above may be changed as appropriate according to an instruction from the operator.

For example, in the first embodiment and the modification examples described above, the projecting function 352 performs the projecting processes in the predetermined range of the brain within the three-dimensional image data. Thus, for example, the projecting function 352 may change the range on which the projecting processes are to be performed, in response to an instruction from the operator. In that situation, for example, the projecting function 352 re-executes the projecting processes every time the range is changed by the operator. Further, every time the projecting processes are re-executed by the projecting function 352, the output function 353 updates the projection images and the measured results being displayed, on the basis of the results of the projecting processes.

For example, in the first embodiment and the modification examples described above, the projecting function 352 extracts regions of MBs or calcification sites and a region of the cortex, on the basis of a predetermined threshold value related to signal values. Thus, for example, the projecting function 352 may change the threshold value used for the segmentation process in response to an instruction from the operator. In that situation, for example, every time the threshold value is changed by the operator, the projecting function 352 re-executes the segmentation process and further re-executes the projecting processes. Further, every time the projecting processes are re-executed by the projecting function 352, the output function 353 updates the projection images and the measured results being displayed, on the basis of the results of the projecting processes.

As explained above, because the operator is allowed to change the predetermined range used in the projecting processes and the set values such as the threshold value used in the segmentation process, the operator is able to set optimal conditions for diagnosing the MBs or the calcification sites, while viewing the projection images and the measured results that are currently displayed.

Further, as for the processes in the first embodiment and the modification examples described above, the plurality of processes may be installed in a single image processing apparatus so that the operator is able to select and execute any of the processes as appropriate.

Further, for example, the projecting function 352 may be configured to receive, from the operator, an operation to select one of the plurality of projecting processes (e.g., the projecting processes illustrated in FIGS. 2, 6, 7, and 8) described in the first embodiment and the modification examples above and to further perform the projecting process selected by the operator.

Further, for example, the output function 353 may be configured to receive, from the operator, an operation to select one of the plurality of projection image output methods (e.g., the output methods illustrated in FIGS. 3, 4, and 9) described in the first embodiment and the modification examples above and to further output the projection images by using the output method selected by the operator.

Further, for example, the output function 353 may be configured to receive, from the operator, an operation to select one of the plurality of measured result output methods (e.g., the output methods illustrated in FIGS. 10 and 11) described in the first embodiment and the modification examples above and to further output the measured results by using the output method selected by the operator.

As explained above, according to the sixth modification example, it is possible to switch between the displays of the projection images and the measured results in response to the instruction from the operator. It is therefore possible to further improve the level of convenience of the image processing apparatus used for diagnosing dementia and the like in the brain.

Seventh Modification Example

Further, in the first embodiment described above, the example is explained in which the projecting function 352 performs the projecting processes by using the three-dimensional image data obtained by the obtaining function 351 without applying any modification thereto; however, possible embodiments are not limited to this example.

For example, the projecting function 352 may perform the projecting processes after performing, on the three-dimensional image data, a process of enhancing the contrast of MBs or calcification sites in the brain. With this arrangement, when the projecting processes are performed, the MBs or the calcification sites are rendered more clearly.

More specifically, the projecting function 352 performs the projecting processes after performing, on the three-dimensional image data obtained by the obtaining function 351, a predetermined process to enhance the contrast of the MBs or the calcification sites occurring in the brain compared to the situation where no such process is performed thereon.

Generally speaking, a tissue having an MB or calcification has a higher level of magnetic susceptibility than a normal tissue does. As a result, it is known that a tissue having an MB or calcification has a larger change in the phase in MR signals. For this reason, for example, the projecting function 352 performs the predetermined process to enhance the contrast of the MBs or the calcification sites in the brain, on the basis of phase information indicating the phases of the MR signals acquired from the brain by the MRI apparatus 100.

For example, the projecting function 352 performs a background phase correcting process to eliminate the phases in the background part on the basis of the phase information, and further performs the process of enhancing the contrast of the MBs or the calcification sites in the brain on the basis of a corrected distribution of phases. In this situation, the background part is the part with normal tissues where no MB or calcification has occurred. The phase of an MR signal generated from the part experiencing an MB or calcification can be calculated by adding a change in the phase caused by the magnetization of the MB or the calcification, to the phase of the normal tissue. Accordingly, by performing the background phase correcting process, it is possible to identify the part having an MB or calcification.

In this situation, for example, the projecting function 352 may calculate a distribution of magnetic susceptibility from a distribution of phases resulting from the phase correcting process and further perform the process of enhancing the contrast of the MBs or the calcification sites in the brain on the basis of the distribution of magnetic susceptibility. In that situation, for example, the projecting function 352 calculates the distribution of magnetic susceptibility by using a Quantitative Susceptibility Mapping (QSM) method by which a magnetic susceptibility map is obtained from a phase map.

For example, when an MB or a calcification site is magnetized, the effect of the magnetization would also be exerted on the tissues in the surroundings thereof. As a result, the effect would also be exerted on changes in the phases of the MR signals generated from the tissues in the surroundings of the MB or the calcification site. In contrast, when the QSM method is used, because the distribution of magnetic susceptibility is obtained for each tissue, it is possible to identify the part representing the MB or the calcification site more accurately. Accordingly, by enhancing the contrast on the basis of the distribution of magnetic susceptibility, it is possible to enhance the contrast of the part representing the MB or the calcification site with a higher level of precision than when enhancing the contrast on the basis of a distribution of phases. As a result, for example, because the contrast between the MBs and the air is enhanced, it is possible to easily extract the MBs while implementing the mIP method, without the need to eliminate the air, the scalp, and the like from the image. As for calcification sites, it is possible to easily extract the calcification sites by using the MIP method.

It is known that, when a substance is magnetized, the level of magnetic susceptibility varies depending on the type of the substance. For this reason, the changes in the phases of the MR signals also vary depending on the type of the substance and may have a positive value or a negative value. For example, with an MB, the phase of an MR signal becomes a negative value. With a calcification site, the phase of an MR signal becomes a positive value. Accordingly, for example, when the diagnosis target is MBs, the projecting function 352 enhances the contrast in the negative direction; and when the diagnosis target is calcification, the projecting function 352 enhances the contrast in the positive direction.

FIGS. 12($i$) to 12($iv$) are drawings illustrating the process of enhancing the contrast of an MB performed by the projecting function 352 according to a seventh modification example. In the following explanation, FIGS. 12($i$) to 12($iv$) are illustrated from top to bottom.

FIG. 12($i$) illustrates an MB 121 occurring in the brain. Further, FIG. 12($ii$) illustrates a distribution of phases of MR signals corresponding to positions on a straight line (indicated with a dotted chain line) passing through the MB 121 illustrated in FIG. 12($i$). More specifically, $\phi_{orig}$ indicates the phases of the MR signals corresponding to the positions on the straight line, whereas $\phi_{back}$ indicates the phases in the background part among the phases $\phi_{orig}$. First, the projecting function 352 calculates the phases $\phi_{back}$ of the background part. For example, the projecting function 352 calculates the phases $\phi_{back}$ of the background part, by applying a low-pass filter having a predetermined intensity to the three-dimensional image data obtained by the obtaining function 351. Alternatively, for example, the projecting function 352 may calculate the phase $\phi_{back}$ of the background part on the basis of data acquired from the same brain for the background phase measuring purpose, with different timing from the timing with which the data for generating the diagnosis-purpose images was acquired.

Subsequently, the projecting function 352 calculates a corrected phase $\phi_{cor}$, by subtracting the phase $\phi_{back}$ of the background part from the phase $\phi_{orig}$ of the MR signals in the three-dimensional image data. Accordingly, for example, as illustrated in FIG. 12($iii$), it is possible to obtain a distribution of phases $\phi_{cor}$ that exhibits zero in the range corresponding to the background part and exhibits a negative value in the range corresponding to the MB.

After that, the projecting function 352 performs the process of enhancing the contrast of the MB in the brain, on the basis of the corrected distribution of phases $\phi_{cor}$ that was calculated. For example, the projecting function 352 enhances the signal values in the MB part, by applying a filter to the three-dimensional image data obtained by the obtaining function 351, the filter being configured in such a manner that the larger is the value of the phase $\phi_{cor}$ in the negative direction, the larger weight is the applied. The filter used in the present example may be, for example, a cosine filter.

Alternatively, instead of performing the process to enhance the contrast on the basis of the corrected distribution of phases $\phi_{cor}$, the projecting function 352 may calculate a distribution of magnetic susceptibility $\chi$ from the corrected distribution of phases $\phi_{cor}$ by implementing a method such as the QSM method. As a result, for example, as illustrated in FIG. 12($iv$), it is possible to obtain the distribution of magnetic susceptibility $\chi$ that exhibits zero in the range corresponding to the background part and exhibits a negative value in the range corresponding to the MB.

After that, the projecting function 352 performs the process of enhancing the contrast of the MBs in the brain on the basis of the calculated distribution of magnetic susceptibility X. For example, the projecting function 352 enhances the signal values in the MB parts by applying a filter to the three-dimensional image data obtained by the obtaining function 351, the filter being configured in such a manner that the larger is the value of the magnetic susceptibility $\chi$ in the negative direction, the larger weight is applied.

FIGS. 13($i$) to 13($iv$) are drawings illustrating the process of enhancing the contrast of a calcification site performed by the projecting function according to the seventh modification example. FIGS. 13($i$) to 13($iv$) are illustrated from top to bottom.

FIG. 13($i$) illustrates a calcification site 131 occurring in the brain. Further, FIG. 13($ii$) illustrates a distribution of phases of MR signals corresponding to positions on a straight line (indicated with a dotted chain line) passing through the calcification site 131 illustrated in FIG. 13($i$). More specifically, $\phi_{orig}$ indicates the phases of the MR signals corresponding to the positions on the straight line, whereas $\phi_{back}$ indicates the phases in the background part among the phases $\phi_{orig}$.

First, similarly to the example described with reference to FIGS. 12($i$) to 12($iv$), after calculating the phase $\phi_{back}$ of the background part, the projecting function 352 calculates a corrected phase $\phi_{cor}$, by subtracting the phase $\phi_{back}$ of the background part from the phase $\phi_{orig}$ of the MR signals in the three-dimensional image data. Accordingly, for example, as illustrated in FIG. 13(iii), it is possible to obtain a distribution of phases $\phi_{cor}$ that exhibits zero in the range corresponding to the background part and exhibits a positive value in the range corresponding to the calcification site.

After that, the projecting function 352 performs the process of enhancing the contrast of the calcification site in the brain, on the basis of the corrected distribution of phases $\phi_{cor}$ that was calculated. For example, the projecting function 352 enhances the signal values in the calcification part, by applying a filter to the three-dimensional image data obtained by the obtaining function 351, the filter being configured in such a manner that the larger is the value of the phase $\phi_{cor}$ in the positive direction, the larger weight is applied. The filter used in the present example may be, for example, a cosine filter.

Alternatively, instead of performing the process to enhance the contrast on the basis of the corrected distribution of phases $\phi_{cor}$, the projecting function 352 may calculate a distribution of magnetic susceptibility $\chi$ from the corrected distribution of phases $\phi_{cor}$ by implementing a method such as the QSM method. As a result, for example, as illustrated in FIG. 13(iv), it is possible to obtain the distribution of magnetic susceptibility $\chi$ that exhibits zero in the range corresponding to the background part and exhibits a positive value in the range corresponding to the calcification site.

After that, the projecting function 352 performs the process of enhancing the contrast of the calcification sites in the brain on the basis of the calculated distribution of magnetic susceptibility x. For example, the projecting function 352 enhances the signal values in the calcification parts by applying a filter to the three-dimensional image data obtained by the obtaining function 351, the filter being configured in such a manner that the larger is the value of the magnetic susceptibility $\chi$ in the positive direction, the larger weight is applied.

According to the seventh modification example described above, the projecting function 352 performs the projecting processes after performing the process of enhancing the contrast of the MBs or the calcification sites in the brain on the three-dimensional image data. With this arrangement, when the projecting processes are performed, the MBs or the calcification sites are rendered more clearly. Consequently, it is possible to improve the level of precision of the diagnosis procedure performed on the brain while using the projection images.

According to the seventh modification example described above, it is possible to obtain images in which the contrast of the MBs is enhanced and images in which the contrast of the calcification sites is enhanced. Thus, for example, it is also acceptable to display the images in which the contrast of the MBs is enhanced and the images in which the contrast of the calcification sites is enhanced, so as to be combined together or so as to be superimposed on each other.

In that situation, as explained in the seventh modification example, the projecting function 352 generates projection images of MBs by implementing the mIP method, after enhancing the contrast of the MBs in the three-dimensional image data of the brain by implementing a method such as the QSM method. Further, as explained in the seventh modification example, the projecting function 352 generates projection images of calcification sites by implementing the MIP method, after enhancing the contrast of the calcification sites in the three-dimensional image data of the brain by implementing a method such as the QSM method. After that, the output function 353 generates fusion images obtained by combining together or superimposing on each other the projection images of the MBs generated by implementing the mIP method and the projection images of the calcification sites generated by implementing the MIP method and further outputs the generated fusion images to the display 340.

Further, although the example with the projecting processes that implement the mIP method or the MIP method is explained above, it is also acceptable, for example, to perform a segmentation process to extract MBs or calcification sites by using the three-dimensional image data in which the contrast of the MBs or the calcification sites is enhanced by implementing a method such as the QSM method.

In that situation, as explained in the seventh modification example, after enhancing the contrast of the MBs or the calcification sites in the three-dimensional image data of the brain by implementing a method such as the QSM method, the projecting function 352 extracts the regions of the MBS or the calcification sites by performing the segmentation process. For example, an image obtained by implementing the QSM method has an absolute value for each of the voxels, as the three-dimensional image data. Thus, for example, after enhancing the contrast of the MBs or the calcification sites by applying a weighting filter or the like to the three-dimensional image data obtained from the QSM method, the projecting function 352 extracts the regions of the MBs or the calcification sites by performing the segmentation process. Alternatively, for example, after extracting the region of a predetermined site such as the brain surface from the three-dimensional image data by performing a segmentation process, the projecting function 352 may generate a volume rendering image of the extracted region of the site and a volume rendering image of the regions of the MBs or the calcification sites and may further output the volume rendering images so as to be superimposed on each other. By performing the segmentation process after enhancing the contrast of the MBs or the calcification sites in the three-dimensional image data in this manner, it is possible to improve the level of precision in the process of extracting the MBs or the calcification sites.

Second Embodiment

In the first embodiment, the exemplary embodiments of the image processing apparatus are explained; however, possible embodiments of the image processing process disclosed in the present application are not limited to those embodiments. For example, the image processing method disclosed in the present application may be implemented by an MRI apparatus. In the following sections, an embodiment implemented by an MRI apparatus will be explained as a second embodiment.

Figure 14:
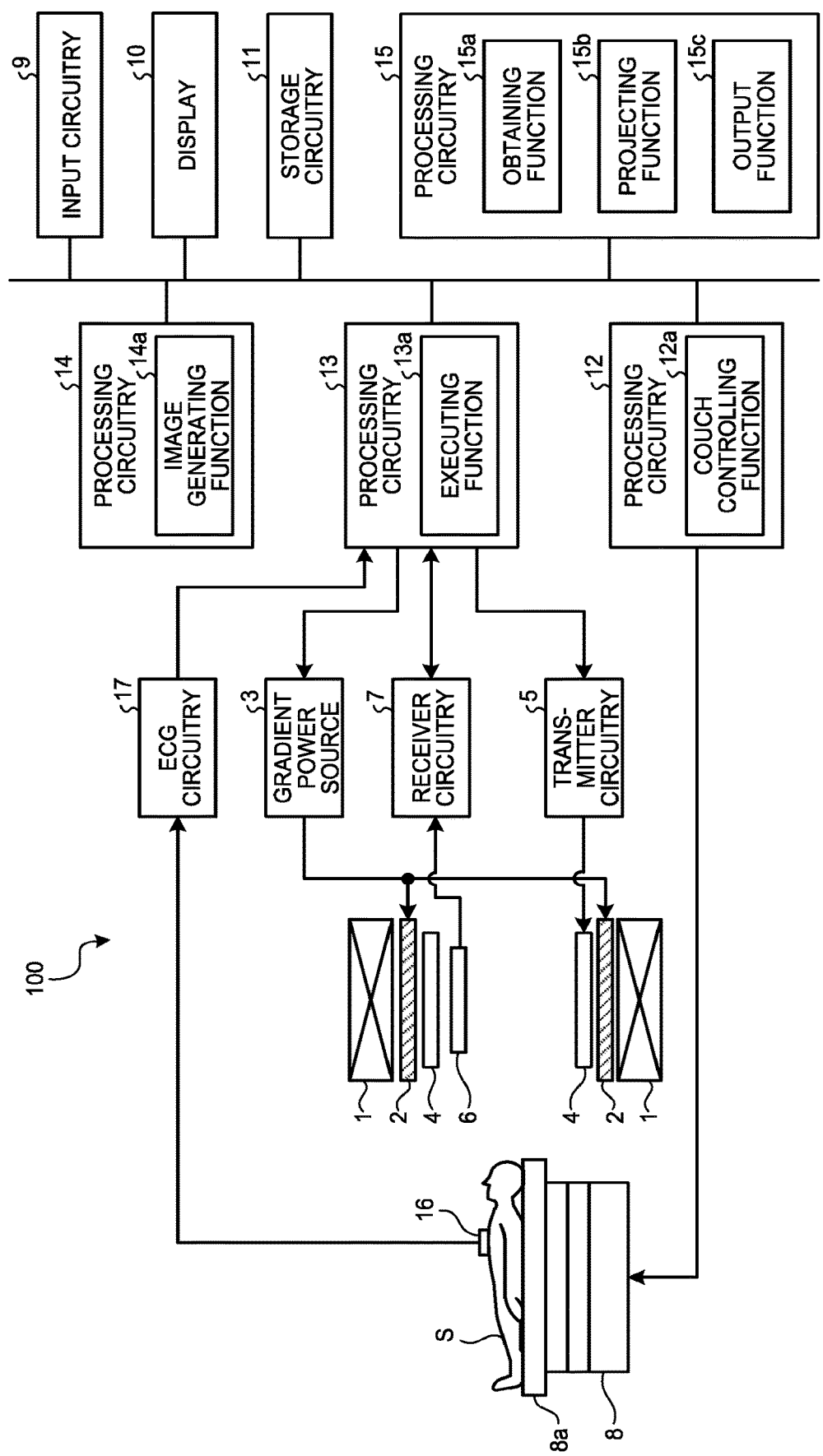
FIG. 14 is a diagram of an exemplary configuration of a Magnetic Resonance Imaging (MRI) apparatus according to a second embodiment.

FIG. 14 is a diagram illustrating an exemplary configuration of an MRI apparatus according to second embodiment. For example, as illustrated in FIG. 14, an MRI apparatus 100 includes a static magnetic field magnet 1, a gradient coil 2, a gradient power source 3, a transmitter coil 4, transmitter circuitry 5, a receiver coil 6, receiver circuitry 7, a couch 8, input circuitry 9, a display 10, storage circuitry 11, processing circuitries 12 to 15, an electrocardiograph (ECG) sensor 16, and an ECG circuitry 17.

The static magnetic field magnet 1 is formed to have a hollow and substantially circular cylindrical shape (which may have an oval cross-section orthogonal to the central axis thereof) and is configured to generate a uniform static magnetic field in an image taking space formed on the inner circumferential side thereof. For example, the static magnetic field magnet 1 may be realized with a permanent magnet, a superconductive magnet, or the like.

The gradient coil 2 is formed to have a hollow and substantially circular cylindrical shape (which may have an oval cross-section orthogonal to the central axis thereof) and is disposed on the inner circumferential side of the static magnetic field magnet 1. The gradient coil 2 includes three coils configured to generate gradient magnetic fields along x-, y-, and z-axes, respectively, that are orthogonal to one another. In this situation, the x-axis, the y-axis, and the z-axis structure an apparatus coordinate system unique to the MRI apparatus 100. For example, the x-axis direction is set in the vertical direction, whereas the y-axis direction is set in the horizontal direction. Further, the z-axis direction is set so as to be the same as the direction of a magnetic flux in the static magnetic field generated by the static magnetic field magnet 1.

By individually supplying an electric current to each of the three coils included in the gradient coil 2, the gradient power source 3 is configured to cause the gradient magnetic fields to be generated along the x-, y-, and z-axes, in the image taking space. The gradient power source 3 is able to cause the gradient magnetic fields to be generated along a read-out direction, a phase-encoding direction, and a slice direction that are orthogonal to one another, by generating the gradient magnetic fields along the x-, y-, and z-axes, as appropriate. In this situation, the axes extending along the read-out direction, the phase-encoding direction, and the slice direction structure a logical coordinate system used for defining slice regions or a volume region serving as a target of an image taking process. In the following sections, the gradient magnetic field generated along the read-out direction will be referred to as a read-out gradient magnetic field; the gradient magnetic field generated along the phase-encoding direction will be referred to as a phase-encoding gradient magnetic field; and the gradient magnetic field generated along the slice direction will be referred to as a slice gradient magnetic field.

The gradient magnetic fields are superimposed on the static magnetic field generated by the static magnetic field magnet 1 and are used for appending spatial position information to magnetic resonance (MR) signals. More specifically, the read-out gradient magnetic field appends position information along the read-out direction to an MR signal, by varying the frequency of the MR signal in accordance with the position in the read-out direction. Further, the phase-encoding gradient magnetic field appends position information in the phase-encoding direction to an MR signal, by varying the phase of the MR signal along the phase-encoding direction. Further, when an image taking region is represented by slice regions, the slice gradient magnetic field is used for determining the orientations, the thicknesses, and the quantity of the slice regions. In contrast, when the image taking region is represented by a volume region, the slice gradient magnetic field appends position information along the slice direction to an MR signal, by varying the phase of the MR signal in accordance with the position in the slice direction.

The transmitter coil 4 is formed to have a hollow and substantially circular cylindrical shape (which may have an oval cross-section orthogonal to the central axis thereof) and is disposed on the inside of the gradient coil 2. The transmitter coil 4 is configured to apply a Radio Frequency (RF) pulse output from the transmitter circuitry 5 to the image taking space.

The transmitter circuitry 5 is configured to output the RF pulse corresponding to a Larmor frequency to the transmitter coil 4. For example, the transmitter circuitry 5 includes an oscillation circuit, a phase selecting circuit, a frequency converting circuit, an amplitude modulating circuit, and an RF amplifying circuit. The oscillation circuit is configured to generate an RF pulse having a resonant frequency unique to a targeted atomic nucleus placed in the static magnetic field. The phase selecting circuit is configured to select a phase of the RF pulse output from the oscillation circuit. The frequency converting circuit is configured to convert the frequency of the RF pulse output from the phase selecting circuit. The amplitude modulating circuit is configured to modulate the amplitude of the RF pulse output from the frequency converting circuit, according to a sinc function, for example. The RF amplifying circuit is configured to amplify the RF pulse output from the amplitude modulating circuit and to output the amplified RF pulse to the transmitter coil 4.

The receiver coil 6 is attached to an examined subject (hereinafter, "patient") S placed in the image taking space and is configured to receive the MR signals emitted from the patient S due to an influence of the RF magnetic field applied by the transmitter coil 4. Further, the receiver coil 6 is configured to output the received MR signals to the receiver circuitry 7. For example, as the receiver coil 6, an exclusively-used coil is employed for each site serving as an image taking target. In this situation, the exclusively-used coil may be, for example, a receiver coil for the head, a receiver coil for the spine, a receiver coil for the abdomen, or the like.

The receiver circuitry 7 is configured to generate MR signal data on the basis of the MR signals output from the receiver coil 6 and to output the generated MR signal data to the processing circuitry 13. For example, the receiver circuitry 7 includes a selecting circuit, a pre-amplifying circuit, a phase detecting circuit, and an analog/digital converting circuit. The selecting circuit is configured to selectively receive an input of the MR signals output from the receiver coil 6. The pre-amplifying circuit is configured to amplify the MR signals output from the selecting circuit. The phase detecting circuit is configured to detect the phases of the MR signals output from the pre-amplifying circuit. The analog/digital converting circuit is configured to generate the MR signal data by converting analog signals output from the phase detector into digital signals and to output the generated MR signal data to the processing circuitry 13.

In the present example, the situation in which the transmitter coil 4 applies the RF pulse so that the receiver coil 6 receives the MR signals is explained; however, possible embodiments of the transmitter coil and the receiver coil are not limited to this example. For instance, the transmitter coil 4 may further have a receiving function to receive the MR signals. Further, the receiver coil 6 may further have a transmitting function to apply an RF magnetic field. When the transmitter coil 4 has the receiving function, the receiver circuitry 7 generates MR signal data also from the MR signals received by the transmitter coil 4. Further, when the receiver coil 6 has the transmitting function, the transmitter circuitry 5 outputs an RF pulse also to the receiver coil 6.

The couch 8 includes a couchtop 8a on which the patient S is placed. When an image taking process is performed on the patient S, the couchtop 8a is inserted into the image taking space formed on the inside of the static magnetic field magnet 1 and the gradient coil 2. For example, the couch 8 is installed in such a manner that the longitudinal direction thereof extends parallel to the central axis of the static magnetic field magnet 1.

The input circuitry 9 is configured to receive operations to input various types of instructions and various types of information from the operator. For example, the input circuitry 9 is realized with a trackball, a switch button, a mouse, a keyboard, a touch panel, and/or the like. The input circuitry 9 is connected to the processing circuitry 15 and is configured to convert each of the input operations received from the operator into an electrical signal and to output the electrical signal to the processing circuitry 15.

The display 10 is configured to display various types of information and various types of images. For example, the display 10 is realized with a liquid crystal monitor, a Cathode Ray Tube (CRT) monitor, a touch panel, or the like. The display 10 is connected to the processing circuitry 15 and is configured to convert data of the various types of information and the various types of images sent thereto from the processing circuitry 15, into display-purpose electrical signals and to output the display-purpose electrical signals.

The storage circuitry 11 is configured to store various types of data therein. For example, the storage circuitry 11 is configured to store therein the MR signal data and image data for each patient S. For example, the storage circuitry 11 is realized with a semiconductor memory device such as a Random Access Memory (RAM), a flash memory, or the like, or a hard disk, an optical disk, or the like.

The processing circuitry 12 includes a couch controlling function 12a. For example, the processing circuitry 12 is realized with a processor. The couch controlling function 12a is connected to the couch 8 and is configured to control operations of the couch 8 by outputting a control-purpose electrical signal to the couch 8. For example, the couch controlling function 12a receives, via the input circuitry 9, an instruction to move the couchtop 8a in a longitudinal direction, an up-and-down direction, or a left-and-right direction from the operator and operates a driving mechanism for the couchtop 8a included in the couch 8 so as to move the couchtop 8a according to the received instruction.

The processing circuitry 13 includes an executing function 13a. For example, the processing circuitry 13 is realized with a processor. The executing function 13a is configured to execute various types of pulse sequences. More specifically, the executing function 13a executes the various types of pulse sequences by driving the gradient power source 3, the transmitter circuitry 5, and the receiver circuitry 7, on the basis of sequence execution data output from the processing circuitry 15.

In this situation, the sequence execution data is information that defines a pulse sequence indicating a procedure performed to acquire the MR signal data. More specifically, the sequence execution data is information that defines: the timing with which the electric current is to be supplied from the gradient power source 3 to the gradient coil 2 and the intensity of the electric current to be supplied; the intensity of an RF pulse current to be supplied from the transmitter circuitry 5 to the transmitter coil 4 and the timing with which the RF pulse current is to be supplied; the timing with which the MR signals are to be detected by the receiver circuitry 7, and the like.

Further, the executing function 13a receives the MR signal data from the receiver circuitry 7 as a result of executing the various types of pulse sequences and stores the received MR signal data into the storage circuitry 11. A set made up of pieces of MR signal data received by the executing function 13a is stored in the storage circuitry 11 as data structuring a k-space as a result of being arranged two-dimensionally or three-dimensionally according to the position information appended by the read-out gradient magnetic field, the phase-encoding gradient magnetic field, and the slice gradient magnetic field described above.

The processing circuitry 14 includes an image generating function 14a. For example, the processing circuitry 14 is realized with a processor. The image generating function 14a is configured to generate an image on the basis of the MR signal data stored in the storage circuitry 11. More specifically, the image generating function 14a generates the image by reading the MR signal data stored in the storage circuitry 11 by the executing function 13a and further performing a reconstructing process such as a post-processing process (i.e., a Fourier transform) on the read MR signal data. Further, the image generating function 14a stores image data of the generated image into the storage circuitry 11.

The processing circuitry 15 is configured to exercise overall control of the MRI apparatus 100 by controlling constituent elements of the MRI apparatus 100. For example, the processing circuitry 15 is realized with a processor. For example, the processing circuitry 15 receives an input of various types of parameters related to the pulse sequence from the operator via the input circuitry 9 and generates the sequence execution data on the basis of the received parameters. After that, the processing circuitry 15 executes various types of pulse sequences by transmitting the generated sequence execution data to the processing circuitry 13. Further, for example, the processing circuitry 15 reads image data of an image requested by the operator from the storage circuitry 11 and outputs the read image to the display 10.

The exemplary configuration of the MRI apparatus 100 according to the second embodiment has thus been explained. The MRI apparatus 100 structured as described above is configured so as to be able to alleviate medical doctors' trouble during the process of diagnosing dementia or the like in the brain that is performed while using medical images.

More specifically, the processing circuitry 15 includes an obtaining function 15a, a projecting function 15b, and an output function 15c.

The obtaining function 15a has the same functions as those of the obtaining function 351 explained in the first embodiment and the modification examples above. It should be noted, however, that the obtaining function 351 according to the first embodiment is configured to obtain the three-dimensional image data of the brain from either the MRI apparatus 100 or the image storing apparatus 200, whereas the obtaining function 15a according to the second embodiment is configured to obtain the three-dimensional image data of the brain from the storage circuitry 11.

The projecting function 15b has the same functions as those of the projecting function 352 explained in the first embodiment and the modification examples above.

The output function 15c has the same functions as those of the output function 353 explained in the first embodiment and the modification examples above.

Further, in the second embodiment, the input circuitry 9, the display 10, and the storage circuitry 11 further have the functions of the input circuitry 330, the display 340, and the storage circuitry 320, respectively, explained in the first embodiment and the modification examples above.

The processing functions included in the processing circuitry 15 have thus been explained. In this situation, for example, the processing functions described above are stored in the storage circuitry 11 in the form of computer-executable programs. The processing circuitry 15 realizes the processing functions corresponding to the computer programs (hereinafter, "programs") by reading the programs from the storage circuitry 11 and executing the read programs. In other words, the processing circuitry 15 that has read the programs has the processing functions illustrated in FIG. 14.

Further, FIG. 14 illustrates the example in which the single processing circuit (the processing circuitry 15) realizes the processing functions such as the obtaining function 15a, the projecting function 15b, and the output function 15c; however, possible embodiments are not limited to this example. For instance, the processing circuitry 15 may be structured by combining a plurality of independent processors together, so that the processing functions are realized as a result of the processors executing the programs. Further, the processing functions included in the processing circuitry 15 may be realized as being distributed or integrated together into single processing circuitry or a plurality of processing circuitries, as appropriate.

With the arrangements described above, according to the second embodiment, it is possible, similarly to the first embodiment, to alleviate medical doctors' trouble during the process of diagnosing dementia or the like in the brain that is performed while using the medical images.

Further, in the embodiments and the modification examples described above, the examples are explained in which the MBs or the calcification sites occurring in the brain serve as the site on which the diagnosing process is performed; however, the diagnosed sites are not limited to these examples. For instance, the image processing method disclosed in the present application is similarly applicable to a situation where a lesion site on the skin or the like serves as a site on which a diagnosing process is performed.

In the second embodiment described above, the embodiments implemented by the MRI apparatus is explained; however, the image processing method disclosed in the present application may be implemented by other image diagnosis apparatuses other than MRI apparatuses. For example, the image processing method disclosed in the present application may similarly be implemented by an X-ray CT apparatus, an ultrasound diagnosis apparatus, a PET apparatus, or the like.

Further, the term "processor" used in the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). It is also acceptable to directly incorporate the programs into the circuit of the processor, instead of storing the programs in the storage circuit. In that situation, the processor realizes the functions by reading and executing the programs incorporated in the circuit thereof. Further, as for the processors according to any of the embodiments, each of the processors may be structured as a single circuit. Alternatively, it is also acceptable to realize the functions thereof by structuring a single processor by combining together a plurality of independent circuits.

According to at least one aspect of the embodiments described above, it is possible to alleviate medical doctors' trouble during the process of diagnosing dementia or the like in the brain that is performed while using the medical images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured:
    to obtain three-dimensional image data of a brain acquired by performing a magnetic resonance imaging process, the three-dimensional image data being image data of a T2*-weighted image, a phase map, a magnetic susceptibility image, a magnetic susceptibility weighted image, a T2* image, or a R2* image;
    to generate a projection image in which a surface of a cross-section of at least a part of the brain is aligned on a plane and a micro bleed or calcification occurring in the brain is rendered, by performing a projecting process on the three-dimensional image data in a range limited on a basis of a shape of the brain; and
    to output the projection image.

2. The image processing apparatus according to claim 1, wherein the processing circuitry is configured to extract a part of the brain in the three-dimensional image data and stretch out a region on the extracted part to generate the projection image in which a surface of a cross-section of the extracted part of the brain is aligned on a plane.

3. The image processing apparatus according to claim 2, wherein the processing circuitry is configured to generate the projection image by performing the projecting process on the converted three-dimensional image data in a range from the surface of the extracted part aligned on the plane to a depth in which the extracted part is included.

4. The image processing apparatus according to claim 1, wherein the range is a range from a surface of the brain to a predetermined depth.

5. The image processing apparatus according to claim 1, wherein the processing circuitry is configured to implement a minimum intensity projection method on the three-dimensional image data.

6. The image processing apparatus according to claim 1, wherein the processing circuitry is configured to extract a cross-section of a cortex part of the brain in the three-dimensional image data and stretch out a region on the extracted cross-section of the cortex part to generate the projection image in which a surface of the extracted cross-section of the cortex part is aligned on a plane.

7. The image processing apparatus according to claim 1, wherein the processing circuitry is configured to enhance contrast of the micro bleed or the calcification occurring in the brain in the three-dimensional image data acquired by a magnetic resonance imaging apparatus.

8. The image processing apparatus according to claim 1, wherein the processing circuitry further outputs a measured result related to the micro bleed or the calcification, on a basis of the three-dimensional image data.

9. The image processing apparatus according to claim 8, wherein the processing circuitry is configured
    to perform projecting processes on the three-dimensional image data from a plurality of mutually-different directions, to generate a plurality of projection images corresponding to the directions, and to output the measured result related to the micro bleed or the calcification that is present in a position designated within the plurality of projection images.

10. The image processing apparatus according to claim 1, wherein the processing circuitry is configured to superimpose the projection image on a predetermined parameter image related to the brain.

11. The image processing apparatus according to claim 1, wherein before generation of the projection image, the processing circuitry is configured to enhance contrast of the micro bleed or the calcification occurring in the brain in the three-dimensional image data.

12. The image processing apparatus according to claim 11, wherein the processing circuitry is configured to enhance the contrast of the micro bleed or the calcification occurring in the brain on a basis of phase information indicating a phase of a magnetic resonance signal acquired from the brain by a magnetic resonance imaging apparatus.

13. The image processing apparatus according to claim 12, wherein the processing circuitry is configured to perform background phase correction to eliminate a phase in a background part on the basis of the phase information and further to enhance the contrast of the micro bleed or the calcification occurring in the brain on the basis of a distribution of phases resulting from the correction.

14. The image processing apparatus according to claim 13, wherein the processing circuitry is configured to calculate a distribution of magnetic susceptibility from the distribution of phases resulting from the correction and further to enhance the contrast of the micro bleed or the calcification occurring in the brain on the basis of the distribution of magnetic susceptibility.

15. The image processing apparatus according to claim 1, wherein the processing circuitry is configured to generate the projection image in which the surface of the cross-section of the at least a part of the brain is aligned on a flat plane.

16. An image processing apparatus comprising processing circuitry configured:
to obtain three-dimensional image data of a brain acquired by performing a magnetic resonance imaging process, the three-dimensional image data being image data of a T2*-weighted image, a phase map, a magnetic susceptibility image, a magnetic susceptibility weighted image, a T2* image, or a R2* image;
to divide a region of the brain in the three-dimensional image data into a plurality of regions so that cortex parts of the brain do not overlap in a projecting direction in each of the plurality of regions;
to generate a plurality of projection images respectively corresponding to the plurality of regions and each rendering a micro bleed or calcification occurring in the brain by performing a projecting process on the three-dimensional image data by using the projecting direction different for each of the plurality of regions; and
to output the plurality of projection images.

17. The image processing apparatus according to claim 16, wherein the processing circuitry is configured to divide the region of the brain into the plurality of regions sectioned according to functions thereof.

18. The image processing apparatus according to claim 16, wherein the processing circuitry is configured to divide the region of the brain into the plurality of regions including a frontal lobe, a parietal lobe, a temporal lobe, and a occipital lobe.

19. The image processing apparatus according to claim 16, wherein the processing circuitry is configured to divide the region of the brain into the plurality of regions sectioned according to a Brodmann's brain map.

20. The image processing apparatus according to claim 16, wherein the processing circuitry is configured to implement a minimum intensity projection method on the three-dimensional image data.

21. An image processing apparatus comprising processing circuitry is configured:
to obtain three-dimensional image data of a brain acquired by performing a magnetic resonance imaging process, the three-dimensional image data being image data of a T2*-weighted image, a phase map, a magnetic susceptibility image, a magnetic susceptibility weighted image, a T2* image, or a R2* image;
to divide a region of the brain in the three-dimensional image data into a plurality of regions sectioned in correspondence with blood-vessel dominant regions;
to generate a projection image rendering a micro bleed or calcification occurring in the brain by performing a projecting process on the three-dimensional image data for each of the plurality of regions; and
to output the projection image.

* * * * *